United States Patent
Vistnes et al.

(10) Patent No.: US 10,744,155 B2
(45) Date of Patent: *Aug. 18, 2020

(54) INHIBITORS OF ADAMTS4 OR ADAMTS5 FOR USE IN PREVENTING OR TREATING CARDIAC REMODELING AND CHRONIC HEART FAILURE

(71) Applicant: Universitetet i Oslo, Oslo (NO)

(72) Inventors: Maria Vistnes, Oslo (NO); Geir Christensen, Oslo (NO); Magnus Aronsen, Oslo (NO); Ida Gjervold Lunde, Oslo (NO); Ivar Sjaastad, Nesbru (NO); Cathrine Rein Carlson, Oslo (NO)

(73) Assignee: UNIVERSITETET I OSLO, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,882

(22) Filed: May 6, 2019

(65) Prior Publication Data
US 2019/0282606 A1    Sep. 19, 2019

Related U.S. Application Data

(63) Continuation of application No. 14/903,624, filed as application No. PCT/EP2014/064761 on Jul. 9, 2014, now Pat. No. 10,322,143.

(30) Foreign Application Priority Data

Jul. 9, 2013   (GB) .................................. 1312311.2

(51) Int. Cl.
*A61K 31/737*   (2006.01)
*A61K 31/4523*   (2006.01)
*A61K 31/453*   (2006.01)

(52) U.S. Cl.
CPC .......... *A61K 31/737* (2013.01); *A61K 31/453* (2013.01); *A61K 31/4523* (2013.01)

(58) Field of Classification Search
None
See application file for complete search history.

(56) References Cited

U.S. PATENT DOCUMENTS

| | | | |
|---|---|---|---|
| 2004/0044194 A1* | 3/2004 | Corcoran | C12N 9/6421 536/23.2 |
| 2006/0004066 A1 | 1/2006 | Morris et al. | |
| 2007/0043066 A1 | 2/2007 | Sum et al. | |
| 2007/0155737 A1 | 7/2007 | Gallagher et al. | |
| 2009/0318342 A1 | 12/2009 | Nagase et al. | |

FOREIGN PATENT DOCUMENTS

| | | |
|---|---|---|
| WO | 98/25597 | 6/1998 |
| WO | 2011/088418 | 7/2011 |

OTHER PUBLICATIONS

International Search Report dated Aug. 19, 2014 in corresponding International Application No. PCT/EP2014/064761.
De Savi, C., et al. Orally active achiral N-hydroxyformamide inhibitors of ADAM-TS4 (aggrecanase-1) and ADAM-TS5 (aggrecanase-2) for the treatment of osteoarthritis. Bioorg Med Chem Lett. 2011. 21(11):3301-3306.
Vistnes, M., et al. Pentosan polysulfate decreases myocardial expression of the extracellular matrix enzyme ADAMTS4 and improves cardiac function in vivo in rats subjected to pressure overload by aortic banding. PLoS One. 2014 9(3):e89621, pp. 1-14.
Chambers, M.G., et al. P81—Pharmacodynamic Assays for ADAMTS-4 and ADAMTS-5 Activity in the Rat Knee. Osteoarthritis and Cartilage. 2005. vol. 13, Suppl. 1, p. S49.
International Preliminary Report on Patentability dated Jan. 12, 2016 in corresponding International (PCT) Application No. PCT/EP2014/064761.
McMurray et al., "ESC Guidelines for the diagnosis and treatment of acute and chronic heart failure 2012", European Journal of Heart Failure, 14(8):803-869 (2012).
Yancy et al., "2013 ACCF/AHA Guideline for the Management of Heart Failure", Circulation, 128:e240-e327 (2013).
Cohn et al., "Cardiac Remodeling—Concepts and Clinical Implications: A Consensus Paper From an International Forum on Cardiac Remodeling", Journal of the American College of Cardiology, 35(3):569-582 (2000).
Hunt et al., "2009 Focused Update Incorporated Into the ACC/AHA 2005 Guidelines for the Diagnosis and Management of Heart Failure in Adults", Circulation, 119(14):e391-e479 (2009).
Zha et al., "ADAMTS4 level in patients with stable coronary artery disease and acute coronary syndromes", Biomedicine & Pharmacotherapy, 64(3):160-164 (2010).
Tanhehco et al., "Reduction of Myocardial Infarct Size After Ischemia and Reperfusion by the Glycosaminoglycan Pentosan Polysulfate", Journal of Cardiovascular Pharmacology, 34(1):153-161 (1999).

(Continued)

*Primary Examiner* — Layla D Berry
(74) *Attorney, Agent, or Firm* — Wenderoth, Lind & Ponack, L.L.P.

(57) ABSTRACT

The present invention provides an inhibitor of an ADAMTS proteoglycanase for use in treating or preventing cardiac remodeling or for use in treating or preventing heart failure in a subject. In particular, the present invention provides an inhibitor of ADAMTS4 or ADAMTS5 for use in treating or preventing cardiac remodeling or chronic heart failure in a subject with cardiac remodeling or with chronic heart failure, or with a condition that may lead to cardiac remodeling and/or chronic heart failure. Also provided is a method of treating or preventing cardiac remodeling or treating or preventing heart failure which method comprises administering to a subject in need thereof a therapeutically effective amount of an inhibitor of an ADAMTS proteoglycanase. Also provided is the use of an inhibitor of an ADAMTS proteoglycanase in the manufacture of a medicament for treating or preventing cardiac remodeling or treating or preventing heart failure.

14 Claims, 19 Drawing Sheets

(56) References Cited

OTHER PUBLICATIONS

Figure 1:
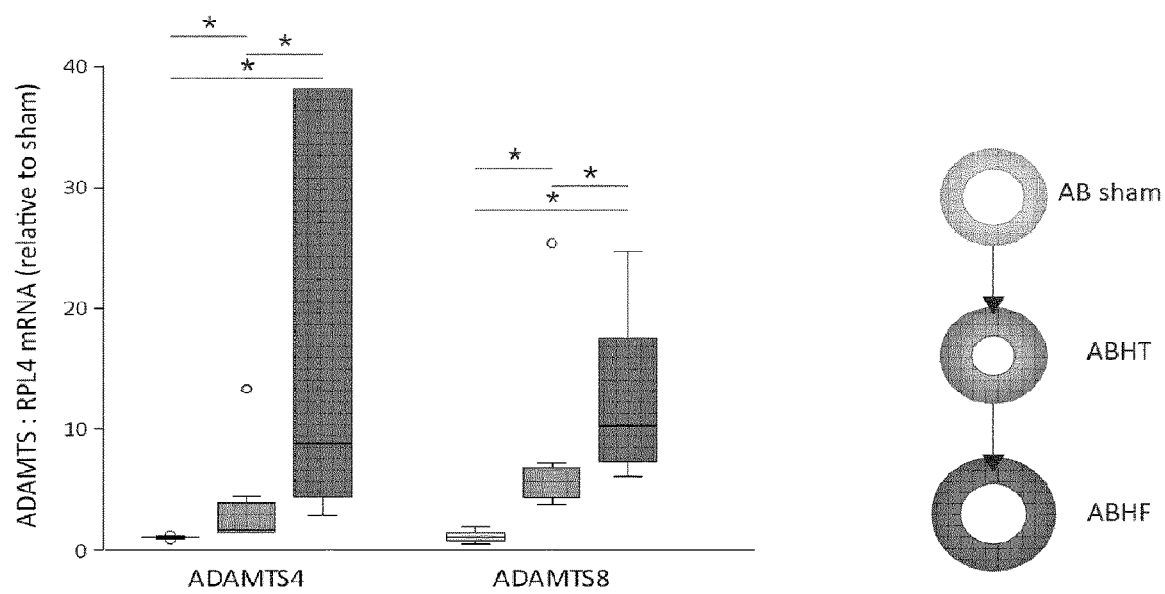
Figure 1:
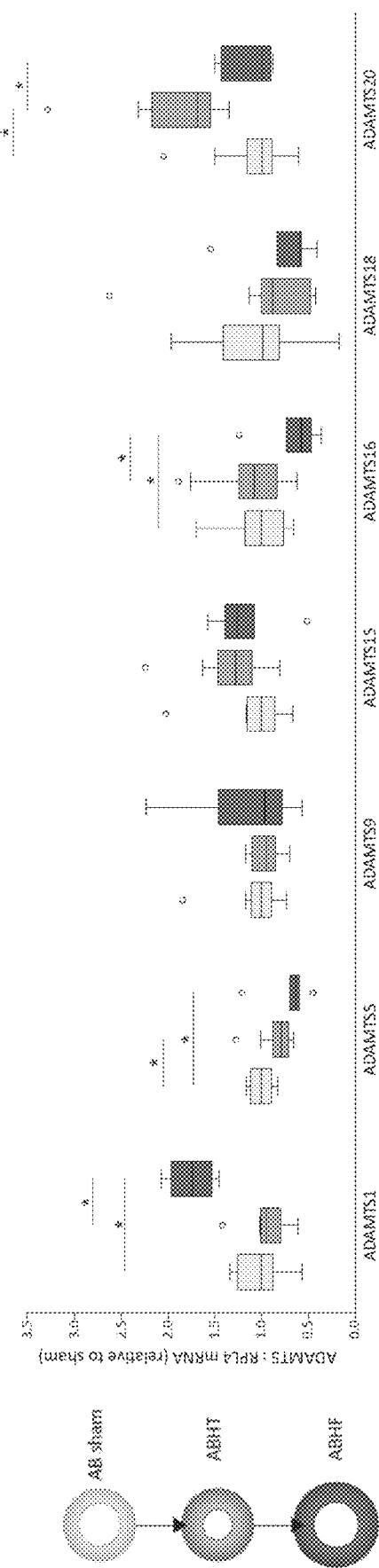

Kloner, "Current State of Clinical Translation of Cardioprotective Agents for Acute Myocardial Infarction", Circulation Research, 113:451-463 (2013).

Kenagy et al., "Accumulation and Loss of Extracellular Matrix During Shear Stress-mediated Intimal Growth and Regression in Baboon Vascular Grafts", Journal of Histochemistry & Cytochemistry, 53(1):131-140 (2005).

Wight, "Versican: a versatile extracellular matrix proteoglycan in cell biology", Current Opinion in Cell Biology, 14(5):617-623 (2002).

Shiomi et al., "Matrix metalloproteinases, a disintegrin and metalloproteinases, and a disintegrin and metalloproteinases with thrombospondin motifs in non-neoplastic diseases", Pathology International, 60(7):477-496 (2010).

Deng et al., "Discovery of Highly Potent and Selective Small Molecule ADAMTS-5 Inhibitors That Inhibit Human Cartilage Degradation via Encoded Library Technology (ELT)", Journal of Medicinal Chemistry, 55(16):7061-7079 (2012).

De Savi et al., "The design and synthesis of novel N-hydroxyformamide inhibitors of ADAM-TS4 for the treatment of osteoarthritis", Bioorganic & Medicinal Chemistry Letters, 21(5):1376-1381 (2011).

Lauer-Fields et al., "Screening of potential ADAMTS-4 inhibitors utilizing a collagen-model FRET substrate", Anal. Biochem., 373(1):43-51 (2008).

Troeberg et al., "Calcium pentosan polysulfate is a multifaceted exosite inhibitor of aggrecanases", The FABES Journal, 22(10):3515-3524 (2008).

Shiozaki et al., "Discovery of (1S,2R,3R)-2,3-Dimethyl-2-phenyl-1-sulfamidocyclopropanecarboxylates: Novel and Highly Selective Aggrecanase Inhibitors", Journal of Medicinal Chemistry, 54:2839-2863 (2011).

Shiozaki et al., "Synthesis and SAR of 2-phenyl-1-sulfonylaminocyclopropane carboxylates as ADAMTS-5 (Aggrecanase-2) inhibitors", Bioorganic & Medicinal Chemistry Letters, 19:6213-6217 (2009).

Yao et al., "Design and Synthesis of a Series of $(2R)-N^4$-Hydroxy-2-(3-hydroxybenzyl)-$N^1$-[(1S,2R)-2-hydroxy-2,3-dihydro-1H-inden-1-yl]butanediamide Derivatives as Potent, Selective, and Orally Bioavailable Aggrecanase Inhibitors", J. Med. Chem., 44:3347-3350 (2001).

Yao et al., "Potent P1' Biphenylmethyl Substituted Aggrecanase Inhibitors", Bioorganic & Medicinal Chemistry Letters, 12:101-104 (2002).

Chockalingam et al., "Elevated aggrecanase activity in a rat model of joint injury is attenuated by an aggrecanase specific inhibitor", Osteoarthritis and Cartilage, 19(3):315-323 (2011).

Gheorghiade et al., "Acute Heart Failure Syndromes: Current State and Framework for Future Research", Circulation, 112(25):3958-3968 (2005).

Lunde et al., "Cardiac O-GlcNAc signaling is increased in hypertrophy and heart failure", Physiol Genomics, 44(2):162-172 (2012).

Sjaastad et al., "Echocardiographic criteria for detection of postinfarction congestive heart failure in rats", J. Appl. Physiol., 89:1445-1454 (2000).

Strand et al., "Innate immune signaling induces expression and shedding of the heparan sulfate proteoglycan syndecan-4 in cardiac fibroblasts and myocytes, affecting inflammation in the pressure-overloaded heart", FEBS Journal, 280(10):2228-2247 (2013).

Didangelos et al., "Novel Role of ADAMTS-5 in Proteoglycan Turnover and Lipoprotein Retention in Atherosclerosis", J. Biol. Chem., 287(23):19341-19345 (2012).

Sandy et al., "Versican V1 Proteolysis in Human Aorta in Vivo Occurs at the $Glu^{441}$-$Ala^{442}$ Bond, a Site That Is Cleaved by Recombinant ADAMTS-1 and ADAMTS-4", The Journal of Biological Chemistry, 276(16):13372-13378 (2001).

Hashimoto et al., "Inhibition of ADAMTS4 (aggrecanase-1) by tissue inhibitors of metalloproteinases (TIMP-1, 2, 3 and 4)", FEBS Letters, 494(3):192-195 (2001).

Gao et al., "ADAMTS4 (Aggrecanase-1) Activation on the Cell Surface Involves C-terminal Cleavage by Glycosylphosphatidyl Inositol-anchored Membrane Type 4-Matrix Metalloproteinase and Binding of the Activated Proteinase to Chondroitin Sulfate and Heparan Sulfate on Syndecan-1", The Journal of Biological Chemistry, 279(11):10042-10051 (2004).

Torre-Amione et al., "Tumor Necrosis Factor-α and Tumor Necrosis Factor Receptors in the Failing Human Heart", Circulation, 93(4):704-711 (1996).

Shioi et al., "Increased Expression of Interleukin-1β and Monocyte Chemotactic and Activating Factor/Monocyte Chemoattractant Protein-1 in the Hypertrophied and Failing Heart With Pressure Overload", Circulation Research, 81(5):664-671 (1997).

Apte, "A disintegrin-like and Metalloproteinase (Reprolysin-type) with Thrombospondin Type 1 Motif (ADAMTS) Superfamily: Functions and Mechanisms", The Journal of Biological Chemistry, 284(46):31493-31497 (2009).

Brooks et al., "Transition from compensated hypertrophy to systolic heart failure in the spontaneously hypertensive rat: Structure, function, and transcript analysis", Genomics, 95(2):94-92 (2010).

Abdel-Aty et al., "Myocardial edema is a feature of Tako-Tsubo cardiomyopathy and is related to the severity of systolic dysfunction: Insights from T2-weighted cardiovascular magnetic resonance", Int. J. Cardiol., 132(2):291-293 (2009).

Laine et al., "Left Ventricular Myocardial Edema: Lymph Flow, Interstitial Fibrosis, and Cardiac Function", Circulation Research, 68(6):1713-1721 (1991).

Davis et al., "Myocardial edema, left ventricular function, and pulmonary hypertension", J. Appl. Physiol., 78(1):132-137 (1995).

Dongaonkar et al., "Myocardial microvascular permeability, interstitial oedema, and compromised cardiac function", Cardiovascular Research, 87(2):331-339 (2010).

Bohl et al., "Advanced methods for quantification of infarct size in mice using three-dimensional high-field late gadolinium enhancement MRI", Am. J. Physiol. Heart. Circ. Physiol., 296(4):H1200-H1208 (2009).

Espe et al., "Novel insight into the detailed myocardial motion and deformation of the rodent heart using high-resolution phase contrast cardiovascular magnetic resonance", Journal of Cardiovascular Magnetic Resonance, 15(1):82 (2013).

Troeberg et al., "Pentosan polysulfate increases affinity between ADAMTS-5 and TIMP-3 through formation of an electrostatically driven trimolecular complex", Biochem. J., 443(1):307-315 (2012).

Takizawa et al., "Calcium pentosan polysulfate directly inhibits enzymatic activity of ADAMTS4 (aggrecanase-1) in osteoarthritic chondrocytes", FEBS Letters, 582(19):2945-2949 (2008).

Chen et al., "Association of serum a disintegrin and metalloproteinase with thrombospodin motif 4 levels with the presence and severity of coronary artery disease", Coronary Artery Disease, 22(8):570-576 (2011).

Zha et al., "Elevated level of ADAMTS4 in plasma and peripheral monocytes from patients with acute coronary syndrome", Clin. Res. Cardiol., 99(12):781-786 (2010).

Zhao et al., "The quantification of ADAMTS4 and 8 expression and selection of reference genes for quantitative real-time PCR analysis in myocardial infarction", Biomedicine & Pharmacotherapy, 65(8):555-559 (2011).

Skrbic et al., "Differential regulation of extracellular matrix constituents in myocardial remodeling with and without heart failure following pressure overload", Matrix Biology, 32:133-142 (2013).

Nuti et al., "Arylsulfonamide inhibitors of aggrecanases as potential therapeutic agents for osteoarthritis: Synthesis and biological evaluation", European Journal of Medicinal Chemistry, 62:379-394 (2013).

Kashiwagi et al., "TIMP-3 Is a Potent Inhibitor of Aggrecanase 1 (ADAM-TS4) and Aggrecanase 2 (ADAM-TS5)", The Journal of Biological Chemistry, 276(16):12501-12504 (2001).

Gilbert et al., "Advances in the development of novel aggrecanase inhibitors", Expert Opinion on Therapeutic Patents, 21(1):1-12 (2011).

Tortorella et al., "Structural and Inhibition Analysis Reveals the Mechanism of Selectivity of a Series of Aggrecanase Inhibitors", The Journal of Biological Chemistry, 284(36):24185-24191 (2009).

(56) References Cited

OTHER PUBLICATIONS

Schroeder et al., "The Broad Spectrum MMP Inhibitor Marimastat Inhibited Early Left Ventricular Dilation following Coronary Artery Ligation in the Rat", Circulation, 104:17 (2001).
Nakamura et al., "Dynamic Induction of ADAMTS1 Gene in the Early Phase of Acute Myocardial Infarction", J. Biochem., 136(4):439-446 (2004).
Onai, Am J Physiol Heart Cirt Physiol 292: H530-H538, 2007.
Guan, Am J Physiol 298: F1276-F1284, 2010.
Cuspidi, Journal of Hypertension 2009, vol. 27, No. 4, pp. 854-860.

* cited by examiner

A

B

C

D

E

A

B

C

INHIBITORS OF ADAMTS4 OR ADAMTS5 FOR USE IN PREVENTING OR TREATING CARDIAC REMODELING AND CHRONIC HEART FAILURE

The present invention relates generally to heart disease. More particularly, the invention relates to the treatment or prevention of cardiac remodeling or the treatment or prevention of chronic heart failure. The invention involves the inhibition of certain proteases/enzymes. Chronic heart failure affects a large number of people worldwide, counting 5-6 million patients in the United States. Chronic heart failure affects mainly the elderly, illustrated by an incidence approaching 10 of 1000 in the population above 65 years of age. Despite current treatment strategies, the prognosis remains poor, with a ~50% 5-year mortality in patients diagnosed with chronic heart failure. Thus, novel and effective treatment strategies are highly warranted.

Heart failure is a clinical syndrome defined by typical symptoms and signs resulting from any structural or functional abnormality of the heart; where the abnormalities may impair the ability to fill or eject blood, and/or lead to failure to deliver sufficient oxygen to meet the requirements of the metabolizing tissues, despite normal filling pressures, or only at the expense of increased filling pressures (ESC Guidelines for the diagnosis and treatment of acute and chronic heart failure. McMurray J J et al. European Heart Journal 2012, 14(8):803-69; 2013 ACCF/AHA Guideline for the Management of Heart Failure Yanzy C W et al. Circulation 2013, 128, e240-e327). Cardiac remodeling usually precedes clinical signs of heart failure, and is defined as "the molecular, cellular and interstitial changes, manifested clinically as changes in size, shape and function of the heart resulting from cardiac load or injury" (Cohn J N et al. JACC 2000. 35(3):569-82). The association between cardiac remodeling and later development of overt heart failure is emphasized in the guidelines from the American Heart Association, defining four stages of heart failure (2013 ACCF/AHA Guideline for the Management of Heart Failure, Yanzy C W et al. Circulation 2013. 128. e240-e327, supra; Hunt S A et al. 2009. 119(14):e391-479). The two first stages (A and B) include asymptomatic patients with risk factors that predispose to development of heart failure. Patients with signs of cardiac remodeling, such as hypertrophy and/or impaired heart function, are designated to stage B, whereas patients with no signs of remodeling are defined to stage A. The two last stages (C and D) include symptomatic patients, where stage C includes patients with current or past symptoms of heart failure associated with underlying structural heart disease, and Stage D includes patients with refractory heart failure requiring advanced treatment strategies.

Cardiac remodeling and chronic heart failure result from disorders that cause persistent increase in cardiac workload, e.g. loss of viable myocardium after myocardial infarction or pressure overload due to aortic stenosis. Common causes of chronic heart failure and cardiac remodeling include, but are not limited to, coronary artery disease, hypertension, cardiomyopathies, valvular diseases, pulmonary disorders and congenital heart defects. Medical treatment inhibiting the maladaptive responses to cardiac load/overload (e.g. treatment introduced before development of cardiac remodeling and chronic heart failure (in AHA's heart failure stage A and B, respectively), or treatment introduced during development or progression of cardiac remodeling and chronic heart failure (in AHA's heart failure stage C and D)) can prevent development or progression of cardiac remodeling and/or heart failure, or at least reduce the morbidity and mortality of chronic heart failure. Current state-of-the-art therapy for chronic heart failure includes inhibitors of the maladaptive neurohormonal activation, such as inhibitors of the β-adrenergic and renin-angiotensin-aldosteron (RAA) system. However, cardiac remodeling and development of chronic heart failure is insufficiently inhibited by these medical therapies.

What is needed in the art are alternative or supplemental therapies, preferably with improved effects or effects complimentary to current conventional therapy, that inhibit the development of cardiac remodeling and/or chronic heart failure (e.g. in patients at risk), particularly those which do not act on the neurohormonal system.

The present invention addresses this need and is based on an evaluation of the proteoglycans versican and aggrecan and their degrading ADAMTS enzymes (ADAMTS proteoglycanases) during cardiac remodeling and development of chronic heart failure, and the surprising finding that inhibition of an ADAMTS versicanase/aggrecanase enzyme (an enzyme which can cleave the proteoglycans versican and aggrecan) leads to improved heart function in appropriate animal models (aortic banding rat model and post-infarction heart failure rat model).

ADAMTS proteoglycanases have previously been studied in atherosclerosis and the acute phase of myocardial infarction (Zha et al. Biomed Pharmacother 2010, 64(3):160-164). Pentosan polysulfate (PPS) has been tested in an acute ischemia/reperfusion model, demonstrating the ability to reduce infarction size when administered during reperfusion (Tanhehco et al. J Cardiovasc Pharm 1999, 34(1), 153-161). Cardioprotective treatment administered during or immediately after revascularization (e.g. Tanhehco et al. supra) aims to counteract ischemia/reperfusion injury and reduce infarct size, where tested approaches include post-conditioning, remote conditioning, cyclosporine and anti-platelet agents (reviewed in Kloner et al. Circulation Research 2013, 113, 451-463). However, the ADAMTS proteoglycanases have not previously been studied in the setting of chronic heart failure and cardiac remodeling. The potential of reducing cardiac remodeling and development of cardiac dysfunction in the setting of persistent cardiac stress, places ADAMTS-inhibition and PPS among therapies that aim to reduce maladaptive responses to overload or injury, without affecting the overload or injury per se. Cardioprotection during reperfusion is regarded as fundamentally different from anti-remodeling therapy administered in the chronic phase after myocardial infarction, in terms of underlying mechanisms, therapeutic targets, time for administration, and indications.

Thus, in a first aspect, the present invention provides an inhibitor of an ADAMTS proteoglycanase for use in treating or preventing cardiac remodeling or for use in treating or preventing heart failure in a subject.

A proteoglycanase is an enzyme which can cleave proteoglycans (e.g. versican, aggrecan or syndecan).

In some embodiments, the ADAMTS proteoglycanase to be inhibited in accordance with the present invention is an ADAMTS versicanase (i.e. an ADAMTS enzyme with versicanase activity).

In some embodiments, the ADAMTS proteoglycanase to be inhibited in accordance with the present invention is an ADAMTS aggrecanase (i.e. an ADAMTS enzyme with aggrecanase activity).

In some embodiments, the ADAMTS proteoglycanase to be inhibited in accordance with the present invention is an ADAMTS proteoglycanase which can cleave syndecan.

In some embodiments, the ADAMTS proteoglycanase to be inhibited is an ADAMTS versicanase or an ADAMTS aggrecanase that is upregulated in a subject (preferably upregulated in the heart) during cardiac remodeling. In some embodiments, the ADAMTS proteoglycanase to be inhibited is an ADAMTS versicanase or an ADAMTS aggrecanase that is upregulated in a subject (preferably upregulated in the heart) upon transition to heart failure, meaning when a remodelled heart develops impaired heart function. In some embodiments, the ADAMTS proteoglycanase to be inhibited is an ADAMTS versicanase or an ADAMTS aggrecanase that is upregulated in a subject (preferably upregulated in the heart) with (i.e. having) chronic heart failure. Preferably, the ADAMTS versicanase or ADAMTS aggrecanase is one that is upregulated in the left ventricle of the heart during cardiac remodeling (e.g. during development of cardiac remodeling), or upon transition to heart failure, or in a subject with chronic heart failure. In some embodiments, the ADAMTS versicanase or ADAMTS aggrecanase is one that is upregulated in the heart (e.g. in the left ventricle) following pressure overload in rats (e.g. following aortic banding in rats). In some embodiments, the ADAMTS versicanase or ADAMTS aggrecanase is one that is upregulated in the heart (e.g. in the left ventricle) following myocardial infarction in rats.

Versican and aggrecan are large hydrophilic proteoglycans located in the extracellular matrix, modifying the structure, volume and hydration of a tissue (Kenagy et al. J. Histochem. Cytochem. 2005, 53:131-140). The versican and aggrecan that are the substrates of the versicanase and aggrecanase enzymes (i.e. the versican and aggrecan that are enzymatically cleaved by the versicanase and aggrecanase, respectively) are preferably located in the extracellular matrix (ECM) of the heart, more preferably the ECM of the myocardium. Versican may exist in several isoforms (V0, V1, V2 and V3 isoforms) (reviewed in Wight, Current Opinion in Cell Biology 2002. 14 (5):617-23). Preferably, the versican that is the subject of the versicanase is the V0 isoform. Other proteoglycans that are substrates of ADAMTS proteoglycanases are also preferably located in the extracellular matrix (ECM) of the heart, more preferably the ECM of the myocardium. Other proteoglycans that are substrates of ADAMTS proteoglycanases are preferably proteoglycans expressed at the cell surface of cells located in the myocardium.

Versican and aggrecan are cleaved by ADAMTS (a disintegrin and metalloprotease with thrombospondin motifs) enzymes; a family of metalloproteases counting 19 members. ADAMTS1, -4, -5, -8, -9, -15, -16, -18, and -20 have known versicanase and/or aggrecanase activity, while the substrates of other ADAMTS enzymes, including ADAMTS6, -10, -12, -17, and -19, are yet to be determined (Shiomi et al. Pathology International 2010. 60(7):477-96).

ADAMTS enzymes (ADAMTS proteoglycanases) that may be inhibited in accordance with the present invention include (but are not limited to) ADAMTS1, -4, -5, -8, -9, -15, -16, -18, and -20. In some embodiments, inhibition of the ADAMTS proteoglycanase ADAMTS4 in accordance with the present invention is preferred. ADAMTS1, -4, -5 and -20 and ADAMTS4 are known to have versicanase activity. ADAMTS1, -4, -5, -8, -9, -15, -16, -18, and -20 are known to have aggrecanase activity (Shiomi et al. supra). ADAMTS6 may also be inhibited.

Preferred ADAMTS versicanases to be inhibited in accordance with the present invention are ADAMTS4, ADAMTS5 and ADAMTS1. Particularly preferred is the ADAMTS4 versicanase. ADAMTS1 is particularly preferred. ADAMTS5 is particularly preferred.

Preferred ADAMTS aggrecanases to be inhibited in accordance with the present invention are ADAMTS5, ADAMTS8, ADAMTS1, ADAMTS15 and ADAMTS4. Particularly preferred are ADAMTS5, ADAMTS8 and ADAMTS4. ADAMTS8 is particularly preferred. ADAMTS4 is particularly preferred. ADAMTS1 is particularly preferred. ADAMTS5 is particularly preferred.

In some embodiments, ADAMTS4 and ADAMTS5 are preferred enzymes to be inhibited in accordance with the present invention.

In some embodiments, preferably the inhibitor inhibits both ADAMTS4 and ADAMTS5.

Any inhibitor of an ADAMTS proteoglycanase as defined above (e.g. of an ADAMTS versicanase and/or of an ADAMTS aggrecanase) may be used in accordance with the present invention. Inhibitory molecules may act at the nucleic acid level, for example they may reduce the expression of an ADAMTS versicanase or ADAMTS aggrecanase gene, thereby, for example, resulting in reduced ADAMTS versicanase or ADAMTS aggrecanase mRNA levels. Preferably, the reduction is a significant reduction, more preferably a statistically significant reduction, preferably with a probability value of ≤0.05. In some embodiments, the inhibitory molecules achieve a reduction of at least 10%, at least 20%, at least 30%, at least 40%, at least 50%, at least 60%, at least 70%, at least 80%, at least 90%, or 100% of ADAMTS versicanase or ADAMTS aggrecanase mRNA levels. In some embodiments, an approximate 80% reduction in ADAMTS versicanase or ADAMTS aggrecanase mRNA levels is achieved.

Inhibitory molecules may alternatively, or in addition, act at the level of the protein and inhibit the functional activity of, for example, the ADAMTS versicanase or ADAMTS aggrecanase enzyme. Inhibition of the ADAMTS versicanase or ADAMTS aggrecanase at the protein level may be, for example, by reducing the level (and/or by altering post-translational modifications) of the ADAMTS versicanase or aggrecanase protein thereby reducing functional activity, and/or by directly inhibiting (reducing) the functional activity of the ADAMTS versicanase or aggrecanase enzyme by, for example, binding to the ADAMTS versicanase or aggrecanase enzyme as an active site inhibitor or as an exosite inhibitor such that versicanase or aggrecanase activity is reduced. Preferably, the reduction in level or functional activity of the ADAMTS versicanase or ADAMTS aggrecanase is a significant reduction, more preferably a statistically significant reduction, preferably with a probability value of ≤0.05. In some embodiments, the inhibitory molecules achieve a reduction of at least 10%, at least 20%, at least 30%, at least 40%, at least 50%, at least 60%, at least 70%, at least 80%, at least 90%, or 100% in the level or functional activity of the ADAMTS versicanase or ADAMTS aggrecanase.

In some embodiments, a reduction in the functional activity of an ADAMTS versicanase is characterized by an increase in the amount (i.e. levels) of full-length versican and/or a decrease in the amount (i.e. levels) of versican cleavage products (e.g. a decrease in the amount of versican cleavage products displaying the DPEEAE neo-epitope, such as the p150 versican DPEEAE fragment or the p70 (70 kDa) versican DPEEAE fragment). In some embodiments, a reduction in the functional activity of an ADAMTS aggrecanase is characterized by an increase in the amount (i.e. levels) of full-length aggrecan and/or a decrease in the amount (i.e. levels) of aggrecan cleavage products (e.g. a decrease in the amount of aggrecan cleavage products displaying the ARG neo-epitope). In all such embodiments, preferably the increase and/or decrease is significant, more preferably statistically significant, preferably with a probability value of ≤0.05. In some embodiments the reduction in the amount of aggrecan or versican cleavage products (e.g. the p150 versican DPEEAE fragment) is at least 10%, at least 20%, at least 30%, at least 40%, at least 50%, at least 60%, at least 70%, at least 80%, at least 90%, or 100%. In some embodiments, an approximately 50% reduction of aggrecan or versican cleavage products (e.g. the p150 versican DPEEAE fragment) is achieved.

The references to "reduce", "reducing", "reduction", "decrease" or "increase" in the above discussions of expression and functional activity mean in comparison to in the absence of the inhibitor.

Suitable ADAMTS versicanase inhibitors or ADAMTS aggrecanase inhibitors may be described in the art. Alternatively, suitable inhibitors can be readily screened for and identified by a person skilled in the art using assays that are routine in the art. By way of example, such a method for identifying a versicanase or aggrecanase inhibitor may comprise: (1) contacting a preparation with a test agent (i.e. a candidate versicanase or aggrecanase inhibitor), wherein the preparation comprises (i) an ADAMTS versicanase or ADAMTS aggrecanase enzyme, or at least a biologically active fragment thereof and optionally a versican or aggrecan substrate; or (ii) a polynucleotide comprising at least a portion of a genetic sequence that regulates the expression of an ADAMTS versicanase enzyme or of an ADAMS aggrecanase (e.g. a promoter and/or an enhancer of an ADAMTS versicanase gene or of an ADAMTS aggrecanase gene), which is operably linked to a reporter gene; and (2) detecting a change in the level and/or functional activity of the ADAMTS versicanase or ADAMTS aggrecanase enzyme, or the level of expression of the reporter gene. Such a level and/or functional activity can be compared to a normal or reference level and/or functional activity in the absence of the test agent. A reduction in the level and/or activity of the ADAMTS versicanase or ADAMTS aggrecanase (as assessed by, for example, analysing for a reduction in the amount of versican cleavage products, e.g. a reduction in the amount of versican cleavage products displaying the DPEEAE neo-epitope such as the p150 versican DPEEAE fragment, or analysing for a reduction in the amount of aggrecan cleavage fragments, e.g. a reduction in the amount of aggrecan cleavage products displaying the ARG neo-epitope), or a reduction in the level of expression of the reporter gene would indicate that, as appropriate, the test agent is an ADAMTS versicanase or an ADAMTS aggrecanase inhibitor.

mRNA levels of an ADAMTS versicanase or an ADAMTS aggrecanase in a cell or tissue (e.g. a cardiac cell or myocardial tissue) after contacting with a test agent can also be monitored using standard techniques in the art (e.g. qRT-PCR). A decrease in an ADAMTS versicanase mRNA level would indicate that the test agent is an ADAMTS versicanase inhibitor. The experimental example section of the present application exemplifies such an approach. A decrease in an ADAMTS aggrecanase mRNA level would indicate that the test agent is an ADAMTS aggrecanase inhibitor.

An example of a method for assessing the functional activity of an ADAMTS versicanase enzyme (the ADAMTS4 versicanase enzyme) after contact with a test agent is provided in the experimental example section of the present application.

Other assays suitable for identifying versicanase inhibitors are also known to a person skilled in the art and may also be used to identify suitable inhibitors for use in accordance with the present invention. Suitable assays are described in Deng et al. (J. Med. Chem. 2012, 55(16):7061-7079), De Savi et al. (Bioorg. & Med. Chem. Let, 2011, 21: (5):1376-1381) and Lauer-Fields et al. (Anal. Biochem. 2008. 373(1):43-51.)

The screening assays disclosed herein may be performed in conventional or high-throughput formats.

The sources for potential agents to be screened include natural sources, such as a cell extracts, and synthetic sources such as chemical compound libraries, or biological libraries such as antibody or peptide libraries.

In some embodiments of the present invention, the inhibitor of an ADAMTS versicanase or ADAMTS aggrecanase is pentosan polysulfate (PPS) (e.g. sodium pentosan polysulfate). Preferably, pentosan polysulfate is an inhibitor of an ADAMTS versicanase (i.e. preferably pentosan polysulfate inhibits versicanase activity). Pentosan polysulfate is a commercially available product, for example from Interfarm AS (Norway). Pentosan polysulfate is described by Troeberg et al. (FASEB J. 2008 October; 22(10):3515-24). Pentosan polysulfate is already used to treat interstitial cystitis in humans (Elmiron®) and athritis in animals (Cartrophen Vet®). Functional analogues of pentosan polysulfate may also be used in accordance with the invention.

In other embodiments, the following compounds, which are also defined in Table 1 of De Savi, et al. ((2011). Bioorg Med Chem Lett. 21:1376-1381) may be used as inhibitors in accordance with the present invention. The synthesis of these compounds is also described in De Savi, et al. ((2011). Bioorg Med Chem Lett. 21:1376-1381).

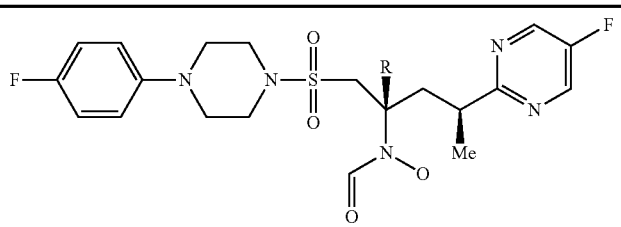

1 R = H
3 R = Me

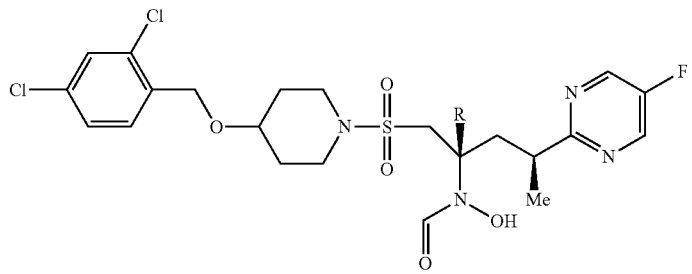

2 R = H
4 R = Me

| Compd | R | ADAM-TS4 IC$_{50}$$^a$ (nM) |
|---|---|---|
| 1 | H | 1.4 |
| 2 | H | 1 |
| 3 | Me | 7.3 |
| 4 | Me | 3.5 |

In other embodiments, the following compounds, which are also defined in Table 2 of De Savi, et al. ((2011). Bioorg Med Chem Lett. 21:1376-1381) may be used as inhibitors in accordance with the present invention. The synthesis of these compounds is also described in De Savi, et al. ((2011). Bioorg Med Chem Lett. 21:1376-1381).

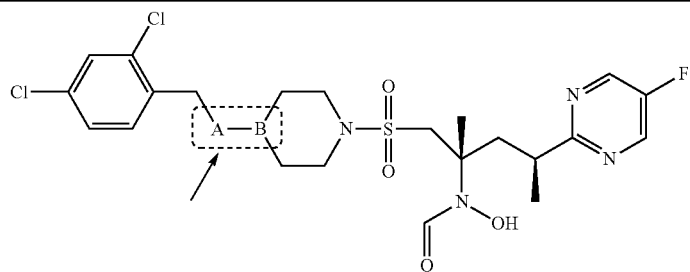

| Compd | A | B | ADAM-TS4 IC$_{50}$ (nM) |
|---|---|---|---|
| 4 | O | C | 3.5 |
| 5 | C | N | 3.8 |
| 6 | C | C | 1.1 |

In other embodiments, the following compounds, which are also defined in Table 3 of De Savi, et al. ((2011). Bioorg Med Chem Lett. 21:1376-1381) may be used as inhibitors in accordance with the present invention. The synthesis of these compounds is also described in De Savi, et al. ((2011). Bioorg Med Chem Lett. 21:1376-1381).

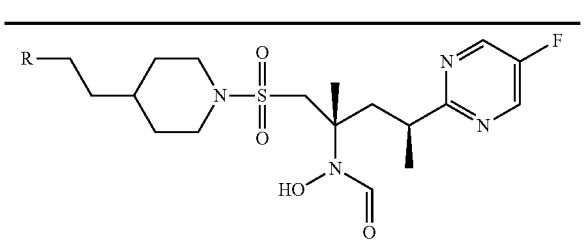

| Compd | R | ADAM-TS4 IC$_{50}$$^a$ (nM) |
|---|---|---|
| 8a | 2-Chloro-4-(trifluoromethyl)phenyl | 0.48 |
| 8b | 4-Chloro-2-methyl-phenyl | 0.36 |
| 8c | 2-Bromo-4-fluoro-phenyl | 0.48 |
| 8d | 2-Chloro-5-fluoro-phenyl | 2.8 |
| 8e | 4-Fluoro-2-(trifluoromethyl)phenyl | 0.52 |
| 8f | 3,5-Dimethylisoxazol-4-yl | 0.69 |
| 8g | 4-Fluoro-2-methyl-phenyl | 0.18 |
| 8h | 2-Methyl-4-trifluoromethyl)phenyl | 0.49 |
| 8i | 2-Cyclopropyl-4-(trifluoromethyl)phenyl | 0.94 |
| 8j | 2,5-Dimethylphenyl | 0.48 |
| 8k | 2,5-Dimethyl-4-pyridyl | 0.43 |
| 8l | 2,5-Dimethyl-3-pyridyl | 1.9 |
| 8m | 3,5-Dimethylisothiazol-4-yl | 0.26 |
| 8n | 4,6-Dimethyl-3-pyridyl | 0.68 |
| 8o | 3-Chloro-5-trifluoromethyl)-2-pyridyl | 4.2 |
| 8p | 3-Methyl-5-(trifluoromethyl-2-pyridyl | 2.1 |
| 8q | 2-Chloro-4-methylsulfonyl-phenyl | 0.57 |
| 8r | 2,5-Dimethylpyrazol-3-yl | 5.4 |

In other embodiments, the following compounds, which are also defined in FIG. 1 and Table 1 of De Savi, et al. ((2011). Bioorg Med Chem Lett. 21:3301-3306) may be used as inhibitors in accordance with the present invention. Of these compounds, compounds 13a, 13b, 13c, 13d, 13f, 13g, 13i, 13j, 13l, 13m and 13n are preferred. For example, in some embodiments of the invention compound 13n may be used and in some embodiments compound 13n is preferred. The synthesis of these compounds is also described in De Savi, et al. ((2011). Bioorg Med Chem Lett. 21:3301-3306).

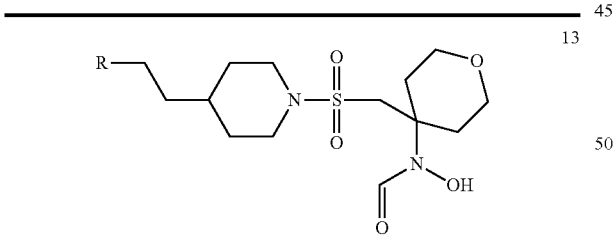

13

| Compds | R | ADAM-TS4 IC$_{50}$, (nM) |
|---|---|---|
| 13a | 4-Chloro-2-methyl-phenyl | 2.7 |
| 13b | 2-Cyclopropyl-4-methylsulfonyl-phenyl | 1.4 |
| 13c | 2-Methyl-4-methylsulfonyl-phenyl | 5.8 |
| 13d | 4-Methyl-3-pyridyl | 110 |
| 13e | Phenyl | 470 |
| 13f | 2-Methylphenyl | 5.6 |
| 13g | 3-Methyl-2-pyridyl | 100 |
| 13h | 2-Methyl-3-pyridyl | 400 |
| 13i | 4,6-Dimethyl-3-pyridyl | 130 |
| 13j | 3,5-Dimethylisothiazol-4-yl | 13 |
| 13k | 2,5-Dimethyl-3-pyridyl | 380 |
| 13l | 2,5-Dimethyl-4-pyridyl | 18 |

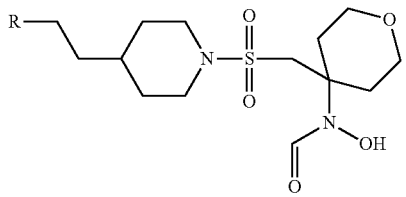

| Compds | R | ADAM-TS4 IC$_{50}$, (nM) |
|---|---|---|
| 13m | 4-Fluoro-2-methyl-phenyl | 4.5 |
| 13n | 3,5-Dimethylisoxazol-4-yl | 26 |

In other embodiments, the following compounds, which are also defined in Table 2 of De Savi, et al. ((2011). Bioorg Med Chem Lett. 21:3301-3306) may be used as inhibitors in accordance with the present invention. The synthesis of these compounds is also described in De Savi, et al. ((2011). Bioorg Med Chem Lett. 21:3301-3306).

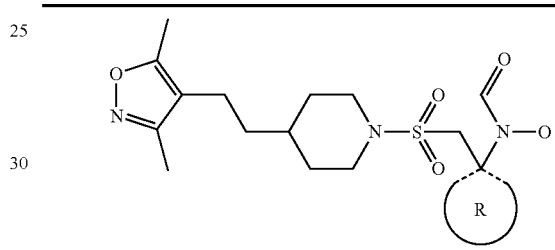

| Compds | R | ADAM-TS4 IC$_{50}$,$^a$ nM |
|---|---|---|
| 14a | 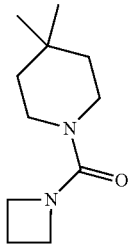 | 11 |
| 14b | 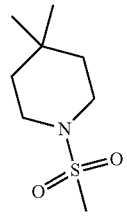 | 29 |
| 14c | 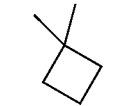 | 51 |
| 14d | 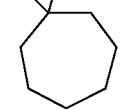 | 48 |

| Compds | R | ADAM-TS4 IC$_{50}$,$^a$ nM |
|---|---|---|
| 14e | (4,4-dimethylpiperidinyl with cyclobutanecarbonyl) | 10 |
| 14f | (4,4-difluoro-1,1-dimethylcyclohexyl) | 20 |
| 14g | (4,4-dimethyltetrahydrothiopyran 1,1-dioxide) | 16 |
| 14h | (1,4,4-trimethylpiperidine N-oxide) | 24 |
| 14i | (2,2,6,6-tetramethyltetrahydropyran) | 9.7 |
| 14j | (1,4,4-trimethylpiperidine) | 19 |
| 14k | (1,1-dimethylcyclopentyl) | 52 |

| Compds | R | ADAM-TS4 IC$_{50}$,$^a$ nM |
|---|---|---|
| 14l | (1,1-dimethylcyclohexyl) | 20 |

In other embodiments, the following compounds, which are also defined in Table 3 of De Savi, et al. ((2011). Bioorg Med Chem Lett. 21:3301-3306) may be used as inhibitors in accordance with the present invention. The synthesis of these compounds is also described in De Savi, et al. ((2011). Bioorg Med Chem Lett. 21:3301-3306).

| Compds | R | ADAM-TS4 IC$_{50}$, nM |
|---|---|---|
| 15a | 4-Fluoro-2-methylphenyl | 1.9 |
| 15b | 2-Methylphenyl | 4.1 |
| 15c | 4-Chloro-2-methylphenyl | 1.2 |
| 15d | 4-Fluoro-2-(trifluoromethyl)phenyl | 8.7 |
| 15e | 2-Methyl-4-(trifluoromethyl) | 1.2 |

In other embodiments, the following compounds, which are also defined in Table 1 (compounds 7b-7d), Table 2 (compounds 8a-8e), Table 3 (compounds 9a-9d), Table 5 (compounds 11a-11e), Table 6 (compounds 12a-12c and 12g-12i), and Table 7 (compounds 13a-13e) of Shiozaki, et al. ((2011). J Med Chem. 54:2839-2863) may be used as inhibitors in accordance with the present invention. Compound 13b is particularly preferred. The synthesis of these compounds is also described in Shiozaki, et al. ((2011). J Med Chem. 54:2839-2863).

wherein R is one of the following:
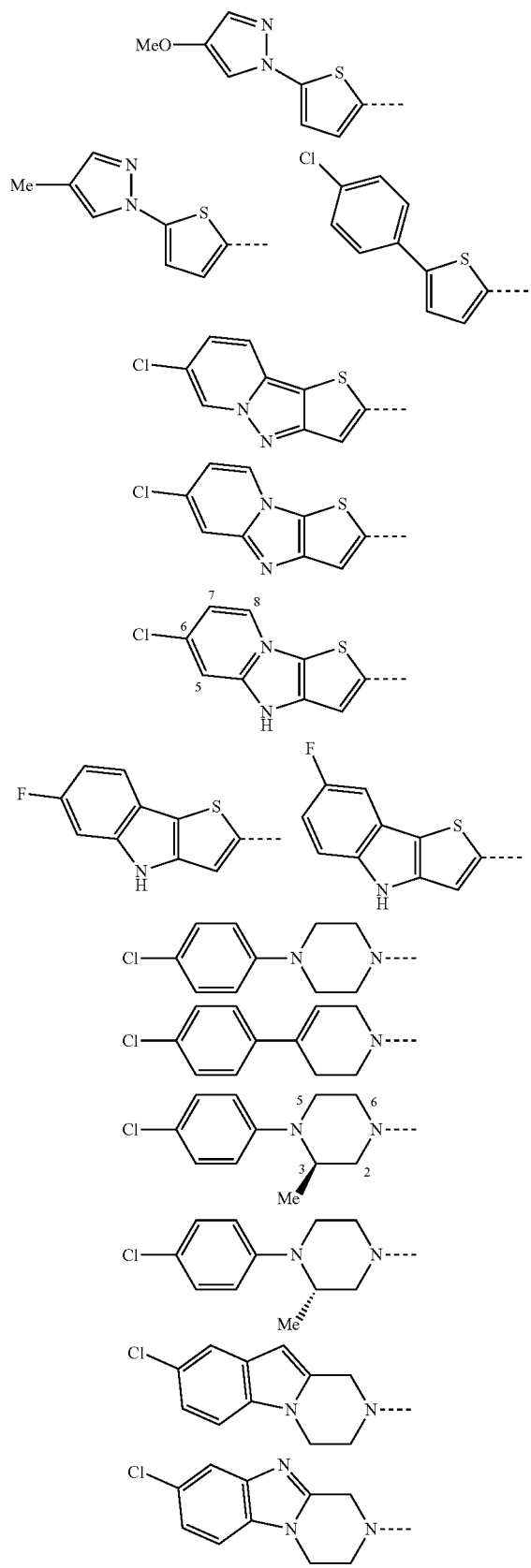
-continued
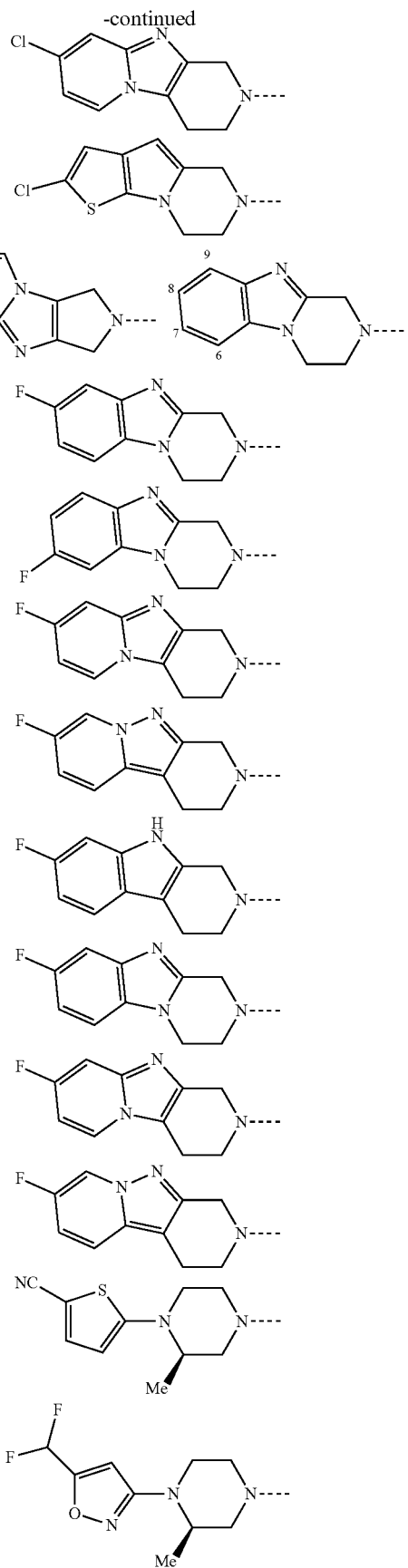

In some embodiments the preferred R group is:

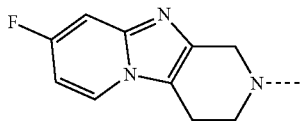

In other embodiments, the following compounds, which are also defined in Table 4 (compounds 10c-10f) of Shiozaki, et al. ((2011). J Med Chem. 54:2839-2863) may be used as inhibitors in accordance with the present invention. The synthesis of these compounds is also described in Shiozaki, et al. ((2011). J Med Chem. 54:2839-2863).

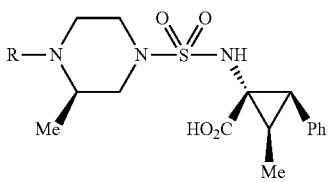

wherein R is one of the following:

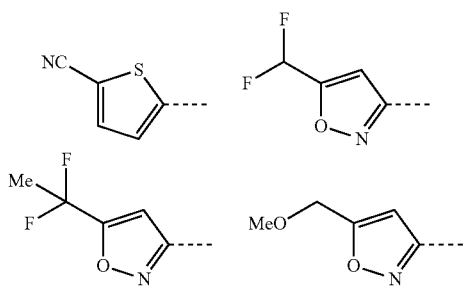

In other embodiments, the following compound, which is also defined in Table 3 (compound 22) of Shiozaki, et al. ((2009). Bioorg Med Chem Lett. 19:6213-6217) may be used as an inhibitor in accordance with the present invention. The synthesis of this compound is also described in Shiozaki, et al. ((2009). Bioorg Med Chem Lett. 19:6213-6217).

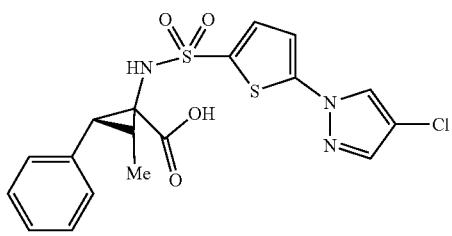

In other embodiments, the following compounds, which are also defined in Table 1 of Shiozaki, et al. ((2009). Bioorg Med Chem Lett. 19:6213-6217) may be used as inhibitors in accordance with the present invention. Of these compounds, compounds 1, 3 and 4 are preferred. In some embodiments, these compounds are used as ADAMTS5 inhibitors in accordance with the present invention. The synthesis of these compounds is also described in Shiozaki, et al. ((2009). Bioorg Med Chem Lett. 19:6213-6217).

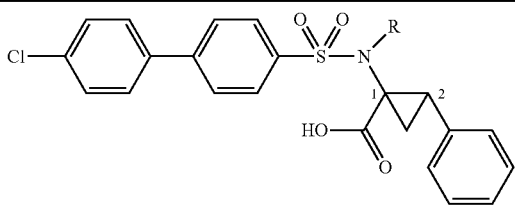

| Compd | Configuration | R | % Inhibition at 0.3 µM | Agg-2 IC$_{50}$ (µM) |
|---|---|---|---|---|
| 1 | (1R,2S) | 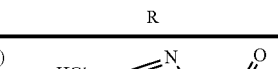 HCl | | 0.073 |
| 2 | (1S,2R) | 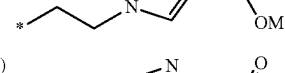 HCl | 18% | |
| 3 | (1R,2S) |  | | 0.210 |
| 4 | (1S,2R) |  | | 0.084 |

In other embodiments, the following compounds, which are also defined in Table 2 of Shiozaki, et al. ((2009). Bioorg Med Chem Lett. 19:6213-6217) may be used as inhibitors in accordance with the present invention. Of these compounds, compounds 5, 6, 8 and 9 are preferred. In some embodiments, these compounds are used as ADAMTS5 inhibitors in accordance with the present invention. The synthesis of these compounds is also described in Shiozaki, et al. ((2009). Bioorg Med Chem Lett. 19:6213-6217).

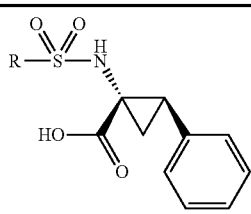

| | | ADAMTS-5 | |
|---|---|---|---|
| Compd | R | % Inhibition at 1.0 µM | IC$_{50}$ (µM) |
| 5 | Cl-phenyl-thiophene | | 0.060 |
| 6 | Cl-phenyl-thiophene | | 0.094 |

| Compd | R | ADAMTS-5 % Inhibition at 1.0 µM | IC$_{50}$ (µM) |
|---|---|---|---|
| 7 | 2-chlorophenyl-thiophene | 48 | |
| 8 | 5-chloropyridinyl-thiophene | | 0.100 |

| Compd | R | ADAMTS-5 % Inhibition at 1.0 µM | IC$_{50}$ (µM) |
|---|---|---|---|
| 9 | Cl-pyrazole-thiophene | | 0.080 |

In other embodiments, the following compounds, which are also defined in Table 3 of Shiozaki, et al. ((2009). Bioorg Med Chem Lett. 19:6213-6217) may be used as inhibitors in accordance with the present invention. Of these compounds, compounds 18, 19, 20, 21 and 22 are preferred. Compound 22 is particularly preferred. In some embodiments, these compounds are used as ADAMTS5 inhibitors in accordance with the present invention. The synthesis of these compounds is also described in Shiozaki, et al. ((2009). Bioorg Med Chem Lett. 19:6213-6217).

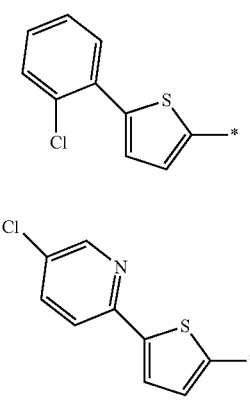

unmethylated • 2-methylated • cis-3-methylated • trans-3-methylated

| Compd | R | Cyclopropane Methylation | ADAMTS-5 IC$_{50}$ (µM) |
|---|---|---|---|
| 5 | 4-Cl-phenyl-thiophene | Unmethylated | 0.060 |
| 18 | | 2-Methyl | 0.010 |
| 19 | | cis-3-Methyl | 0.021 |
| 20[a] | | trans-3-Methyl | 0.120 |
| 9 | Cl-pyrazole-thiophene | Unmethylated | 0.080 |
| 21 | | 2-Methyl | 0.032 |
| 22 | | cis-3-Methyl | 0.0074 |

[a]Racemic compound

In other embodiments, the following compounds, which are also defined in Table 1 of Yao et al. ((2001). J Med Chem 44:3347-3350) may be used as inhibitors in accordance with the present invention. Of these compounds, compounds 7, 8 and 11 are preferred. The synthesis of these compounds is also described in Yao et al. ((2001). J Med Chem 44:3347-3350).

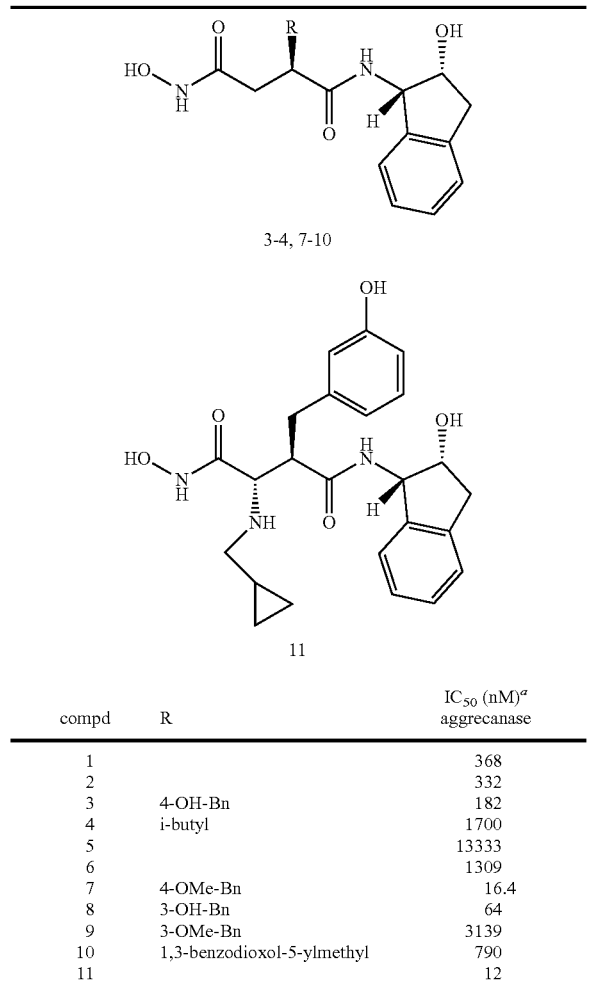

3-4, 7-10

11

| compd | R | $IC_{50}$ (nM)[a] aggrecanase |
|---|---|---|
| 1 |  | 368 |
| 2 |  | 332 |
| 3 | 4-OH-Bn | 182 |
| 4 | i-butyl | 1700 |
| 5 |  | 13333 |
| 6 |  | 1309 |
| 7 | 4-OMe-Bn | 16.4 |
| 8 | 3-OH-Bn | 64 |
| 9 | 3-OMe-Bn | 3139 |
| 10 | 1,3-benzodioxol-5-ylmethyl | 790 |
| 11 |  | 12 |

In other embodiments, the following compounds, which are also defined in Table 1 of Yao, et al. ((2002). Bioorg Med Chem Lett. 12:101-104) may be used as inhibitors in accordance with the present invention. The synthesis of these compounds is also described in Yao, et al. ((2002). Bioorg Med Chem Lett. 12:101-104).

2a-n

| Compd | R | $IC_{50}$ (nM)[a,b] Aggrecanase |
|---|---|---|
| 1 | — | 64 |
| 2a | H | 9.8 |
| 2b | 2-Me | 11.6 |
| 2c | 2-Cl | 32 |
| 2d | 2-MeO | 3.4 |
| 2e | — | 239 |
| 2f | 2-$^t$BuNHSO$_2$ | 75 |
| 2g | 2-HOCH$_2$ | 144 |
| 2h | 3-Me | 11.5 |
| 2i | 3-i-Pr | 216 |
| 2j | — | 1.5 |
| 2k | 3-MeO | 3.7 |
| 2l | 3-F | 2.0 |
| 2m | 3-NO$_2$ | 5.5 |
| 2n | 3-MeSO$_2$NH | 1.5 |

Figure 2:
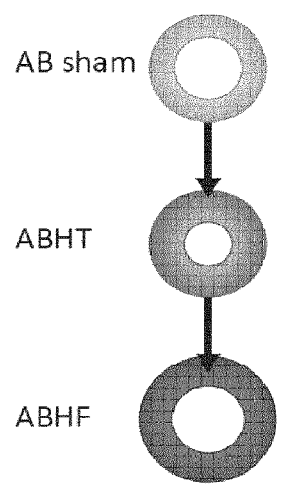
Figure 2:
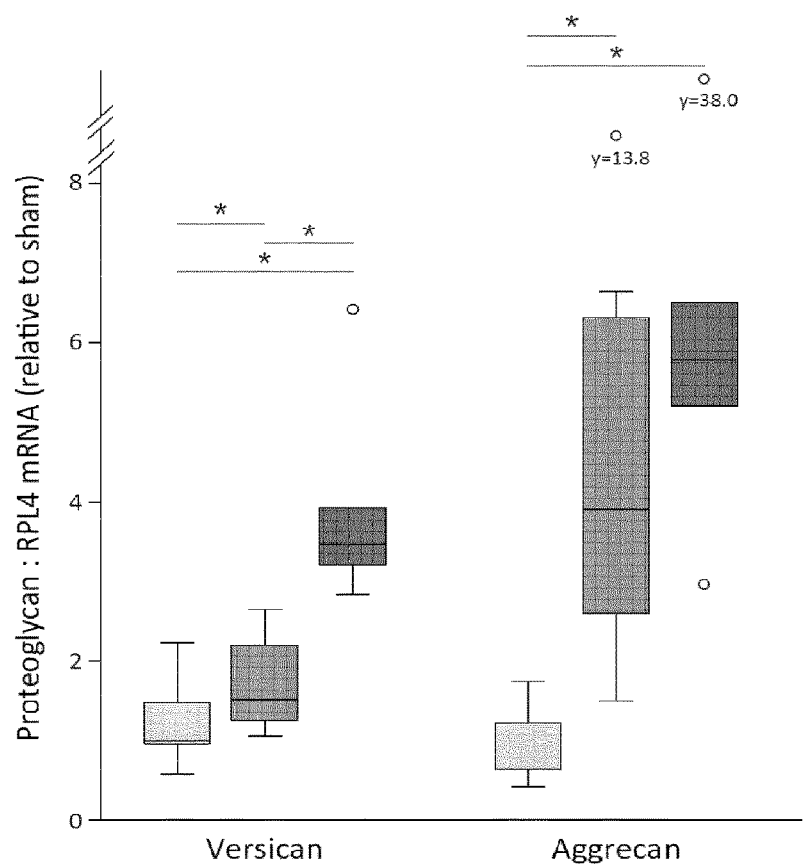

In other embodiments, the following compounds, which are also defined in FIG. 2 of Deng, et al. ((2012). J. Med. Chem, 55(16):7061-79) may be used as inhibitors in accordance with the present invention. In some embodiments, these compounds are used as ADAMTS5 inhibitors in accordance with the present invention. The synthesis of these compounds is also described in Deng, et al. ((2012). J. Med. Chem, 55(16):7061-79).

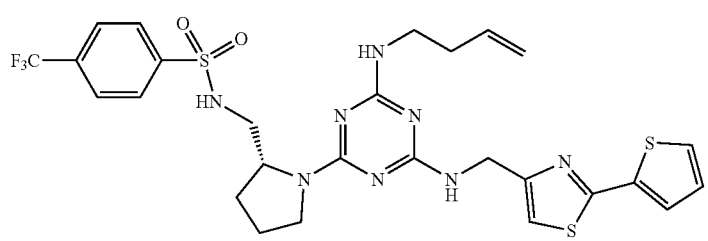 [SMILES: C=CCCNc1nc(NCc2csc(-c3cccs3)n2)nc(N2CCC[C@@H]2CNS(=O)(=O)c2ccc(C(F)(F)F)cc2)n1]

7

-continued

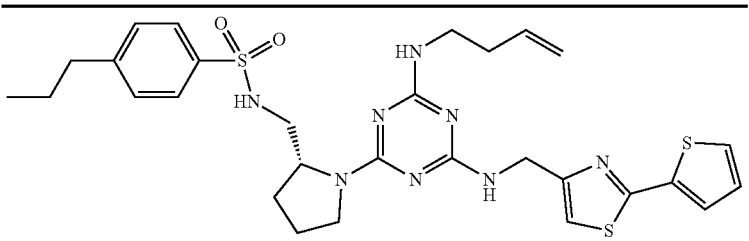

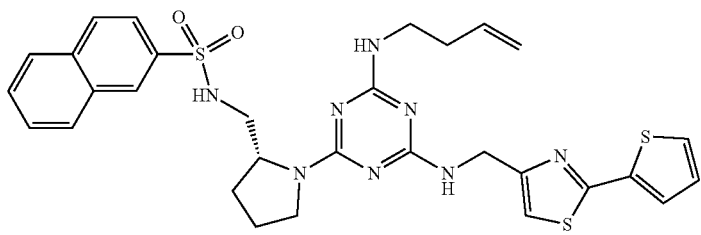 [SMILES: C=CCCNc1nc(NCc2csc(-c3cccs3)n2)nc(N2CCC[C@@H]2CNS(=O)(=O)c2ccc3ccccc3c2)n1]

| Compd | ADAMTS-5 IC$_{50}$ (µM)$^a$ |
|---|---|
| 7 | 0.050 |
| 8 | 0.030 |
| 9 | 0.040 |

In other embodiments, the following compounds, which are also defined in Table 1 of Deng, et al. ((2012). J. Med. Chem, 55(16):7061-79) may be used as inhibitors in accordance with the present invention. Of these compounds, compounds 7, 12a, 12b, 12c, 13a, 13c, 13e, 13g, 13h and 13i are preferred. In some embodiments, these compounds are used as ADAMTS5 inhibitors in accordance with the present invention. The synthesis of these compounds is also described in Deng, et al. ((2012). J. Med. Chem, 55(16): 7061-79).

| Compd | $R_1$ | TS-5 IC$_{50}$ (µM) |
|---|---|---|
| 7 | HN—CH$_2$CH$_2$CH=CH$_2$ | 0.05 |
| 12a | HN—CH$_2$CH$_2$CH$_2$CH$_3$ | 0.24 |
| 12b | HN—CH$_2$-cyclopropyl | 0.11 |
| 12c | NH— | 0.39 |

-continued

| Compd | R₁ | TS-5 IC₅₀ (μM) |
|---|---|---|
| 12d | —OH | 5.30 |
| 12e | —H | 3.50 |

13

[Structure: 4-propyl-benzenesulfonamide-CH₂-(S)-pyrrolidine-N-triazine(R₁)-NH-CH₂-(2-phenylthiazole)]

| Compd | R₁ | TS-5 IC₅₀ (μM) |
|---|---|---|
| 13a | —HN-propyl | 0.05 |
| 13b | —N(CH₃)-propyl | >10 |
| 13c | —HN-isobutyl | 0.12 |
| 13d | —HN-CH₂CH₂-cyclopropyl | 3.8 |
| 13e | —HN-cyclopropyl | 0.07 |
| 13f | —HN-cyclopentyl | 1.60 |
| 13g | —HN-CH₂CH₂-CN | 0.09 |
| 13h | —HN-CH₂CH₂-OH | 0.26 |
| 13i | —HN-CH₂CH₂-OCH₃ | 0.21 |

-continued

| | | |
|---|---|---|
| 13j | 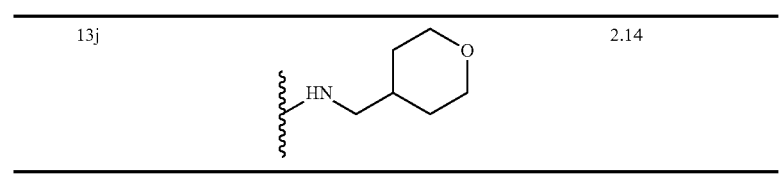 | 2.14 |

In other embodiments, the following compounds, which are also defined in Table 2 of Deng, et al. ((2012). J. Med. Chem, 55(16):7061-79) may be used as inhibitors in accordance with the present invention. Of these compounds, compounds 14a, 14d, 15d and 15f are preferred. In some embodiments, these compounds are used as ADAMTS5 inhibitors in accordance with the present invention. The synthesis of these compounds is also described in Deng, et al. ((2012). J. Med. Chem, 55(16):7061-79).

14

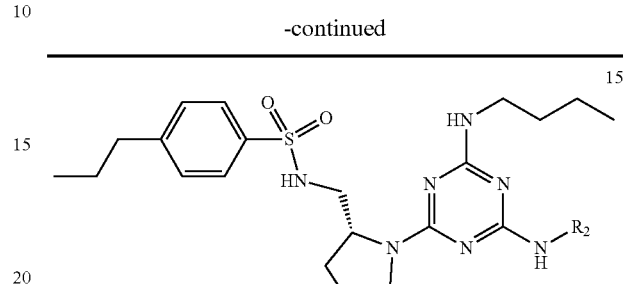

| Compd | $R_2$ | TS-5 IC$_{50}$ (µM) |
|---|---|---|
| 7 | | 0.05 |
| 14a | | 0.06 |
| 14b | | >10 |
| 14c | | >10 |
| 14d | | 0.43 |
| 14e | | 0.87 |
| 12a | | 0.24 |
| 15a | | 1.17 |
| 15b | | >10 |
| 15c | | 4.1 |
| 15d | | 0.41 |
| 15e | | >10 |
| 15f | | 0.03 |
| 15g | | >10 |

-continued

| Compd | R | TS-5 IC$_{50}$ (µM) |
|---|---|---|
| 15h | cyclopentylmethyl | >10 |
| 15i | cyclopropylmethyl | 6.5 |
| 15j | isobutyl | 5.8 |

In other embodiments, the following compounds, which are also defined in Table 4 of Deng, et al. ((2012). J. Med. Chem, 55(16):7061-79) may be used as inhibitors in accordance with the present invention. Of these compounds, compounds 14a, 19c, and 19d are preferred. In some embodiments, these compounds are used as ADAMTS5 inhibitors in accordance with the present invention. The synthesis of these compounds is also described in Deng, et al. ((2012). J. Med. Chem, 55(16):7061-79).

19

| Compd | R$_4$ | TS-5 IC$_{50}$ (µM) |
|---|---|---|
| 14a | 4-(trifluoromethyl)phenyl | 0.06 |
| 19a | 3-(trifluoromethyl)phenyl | >10 |
| 19b | 2-(trifluoromethyl)phenyl | >10 |
| 19c | 4-methoxyphenyl | 0.05 |
| 19d | phenyl | 0.23 |
| 19e | cyclopropyl | >10 |

In some embodiments, of the compounds of Deng, et al. ((2012). J. Med. Chem, 55(16):7061-79) set out above, compounds 7, 8, 9, 13e, 13g and 15f are preferred compounds for use as inhibitors in accordance with the present invention. In some embodiments, compound 13e is particularly preferred. In some embodiments, these compounds are used as ADAMTS5 inhibitors in accordance with the present invention.

In some embodiments, the drug marimastat may be used as an inhibitor in accordance with the present invention. Marimastat is a commercially available product (e.g. from Sigma-Aldrich). The CAS code for marimastat is CAS 154039-60-8.

In some embodiments of the present invention, the compound AGG-523 (Chockalingam et al. Osteoarthritis Cartilage 2011. 19(3):315-23) may be used as an inhibitor in accordance with the present invention. AGG-523 is Pfizer compound. AGG-523 is a reversible, non-hydroxamate, zinc-binding selective inhibitor of ADAMTS4 and ADAMTS5 that was developed by structure-based design (US Patent Publication No. 2007/0043066).

In accordance with the present invention, the compounds defined above may be used as inhibitors of ADAMTS proteoglycanases (i.e. the compounds inhibit proteoglycan cleaving activity).

In some embodiments, the compounds defined above are inhibitors of ADAMTS versicanases (i.e. the compounds inhibit versicanase activity).

In some embodiments, the compounds defined above are inhibitors of ADAMTS aggrecanases (i.e. the compounds inhibit aggrecanase activity).

In some embodiments, the versicanase and/or aggrecanase inhibitor used in accordance with the present invention is selected from the group consisting of pentosan polysulfate (e.g. sodium pentosan polysulfate), the compounds defined by the structural formulae above, marimastat and AGG-523.

In preferred embodiments of the present invention, the inhibitor of an ADAMTS versicanase enzyme as defined above is pentosan polysulfate (PPS). In such embodiments, preferably the ADAMTS versicanase is ADAMTS4. In another such embodiment, preferably the ADAMTS versicanase is ADAMTS5.

Functional analogues of the above inhibitors may also be employed.

Other ADAMTS versicanase inhibitors or ADAMTS aggrecanase inhibitors that may be used in accordance with the present invention include antisense DNA or RNA molecules, RNAi molecules, ribozymes, shRNA molecules, siRNA molecules, miRNA molecules, and the like which are directed against a gene (or a transcript of a gene) encoding an ADAMTS versicanase or ADAMTS aggrecanase enzyme as defined above. Preferred versicanase and aggrecanase enzymes for inhibition in this way are as described elsewhere herein. The ADAMTS4 gene (or transcript) is a particularly preferred versicanase/aggrecanase enzyme for inhibition by such nucleic acid based inhibitory molecules. Once a versicanase or aggrecanase target for inhibition has been selected (e.g. ADAMTS4), it is routine in the art to design and synthesise such nucleic acid based inhibitory molecules, based on the nucleic acid sequence of the inhibitor's target. Nucleic acid sequences of ADAMTS versicanases and ADAMTS aggrecanases are known in the art.

Other ADAMTS versicanase inhibitors or ADAMTS aggrecanase inhibitors that may be used in accordance with the present invention are antibodies, or antigen-binding fragments thereof, which bind to an ADAMTS versicanase or ADAMTS aggrecanase as defined above. It is well known in the art that upon binding of an antibody to its protein (antigen) target, the function of that protein target can be inhibited. Preferred versicanase and aggrecanase enzymes for inhibition in this way are as described elsewhere herein. An inhibitory antibody against the ADAMTS4 versicanase/aggrecanase enzyme is preferred. Once an ADAMTS versicanase or an ADAMTS aggrecanase enzyme has been selected, standard techniques in the art (e.g. phage display) can be used to generate antibodies against that enzyme and routine tests can be performed to subsequently identify antibodies with inhibitory activity.

The nucleic acid based inhibitors and antibody inhibitors described above preferably achieve a significant reduction in the level or functional activity of the ADAMTS versicanase or ADAMTS aggrecanase, more preferably a statistically significant reduction, preferably with a probability value of ≤0.05. In some embodiments, the inhibitory molecules achieve a reduction of at least 10%, at least 20%, at least 30%, at least 40%, at least 50%, at least 60%, at least 70%, at least 80%, at least 90%, or 100% in the level or functional activity of the ADAMTS versicanase or ADAMTS aggrecanase.

In some embodiments of the invention, selective ADAMTS inhibitors (e.g. selective ADAMTS4 or selective ADAMTS5 inhibitors) are preferred. In some embodiments, a selective ADAMTS inhibitor inhibits one or more (e.g. two or more) ADAMTS enzymes (e.g. inhibits ADAMTS4 and ADAMTS5).

In some embodiments, a selective inhibitor is an inhibitor with higher activity (potency) for ADAMTS proteoglycanases (e.g. ADAMTS4 and/or ADAMTS5) than for other enzymes or other classes of enzymes. In some embodiments, a selective inhibitor is an inhibitor with higher activity (potency) for ADAMTS proteoglycanases (e.g. ADAMTS4 and/or ADAMTS5) than for matrix metalloproteinases (MMPs).

Accordingly, in some embodiments broad-spectrum inhibitors such as those which inhibit other classes of enzymes or proteases (e.g. matrix metalloproteinases, MMPs) are not preferred, for example the broad spectrum MMP inhibitor marimastat is not preferred. Thus, in certain preferred embodiments, marimastat or another broad spectrum MMP inhibitor, or other broad spectrum inhibitor is not used as an inhibitor in accordance with the present invention.

In some embodiments, preferably the inhibitors have higher activity (potency) towards ADAMTS proteoglycanases (e.g. ADAMTS4 or ADAMTS5) than they have towards matrix metalloproteinases (MMPs).

In some preferred embodiments, an inhibitor (e.g. selective inhibitor) has at least 5 times, at least 7 times, at least 10 times, at least 20 times, at least 50 times, at least 100 times, at least 200 times, at least 500 times, or at least 1000 times higher activity (potency) (e.g. 5-50 times, 10-30 times or 5 to 1000 times higher) towards ADAMTS proteoglycanases (e.g. ADAMTS4 or ADAMTS5) than towards other enzymes or other classes of enzymes (e.g. MMPs).

In some embodiments inhibitors which have higher activity (potency) towards other enzymes or other classes of enzymes (e.g. MMPs) than towards ADAMTS proteoglycanases are not employed. By way of example, in some embodiments inhibitors which have at least 5 times (e.g. 5-50 times or 5-1000 times), at least 7 times, at least 10 times (e.g. 10-30 times), at least 20 times, at least 50 times, at least 100 times, at least 200 times, at least 500 times, or at least 1000 times higher potency towards other enzymes or other classes of enzymes (e.g. MMPs) than towards ADAMTS proteoglycanases (e.g. ADAMTS4 or ADAMTS5) are not preferred.

In some embodiments, preferably a higher activity (potency) means a significantly higher activity (potency), more preferably a statistically significant higher activity (potency), preferably with a probability value of ≤0.05.

Inhibitory activities (potency) can be assessed (and optionally be quantified) by any convenient means in the art and the skilled person is aware of suitable assays. For example, activity (potency) can be assessed (and optionally quantified) by determining the $IC_{50}$ or $K_i$ (inhibitory constant) of a given inhibitor for its target. Thus, the inhibitory activity (potency) of an inhibitor can be judged by its $IC_{50}$ or $K_i$ values. The relative activities (potencies) of two or more inhibitors can be established by comparing the $IC_{50}$ or $K_i$ values of said inhibitors to each other.

Without wishing to be bound by theory, it is believed that ADAMTS enzymes (e.g. ADAMTS4) are a more promising target for inhibition than MMPs because, as opposed to many MMPs, ADAMTS enzymes (e.g. ADAMTS4) have fewer substrates and cleave proteoglycans (especially versican, aggrecan and syndecan-4) without collagenase effects.

As outlined above, the present invention provides the above described inhibitors for use in treating or preventing cardiac remodeling or heart failure in a subject. For example, the present invention provides one or more of the specific compounds described above (e.g. PPS) for use in treating or preventing cardiac remodeling or heart failure in a subject.

In one embodiment, the present invention provides an inhibitor of ADAMTS4 or ADAMTS5 for use in treating or preventing cardiac remodeling or chronic heart failure in a subject with cardiac remodeling or with chronic heart failure, or with a condition that may lead to cardiac remodeling and/or chronic heart failure.

In one embodiment, the present invention provides an inhibitor of ADAMTS4 or ADAMTS5 for use in treating or preventing cardiac remodeling or chronic heart failure in a subject with cardiac remodeling or with chronic heart failure.

In one embodiment, the present invention provides an inhibitor of ADAMTS4 or ADAMTS5 for use in treating or preventing cardiac remodeling or chronic heart failure in a subject with a condition that may lead to cardiac remodeling and/or chronic heart failure.

In certain embodiments, the preventing of cardiac remodeling or chronic heart failure is in a subject with cardiac remodeling or with chronic heart failure.

Cardiac remodeling is a term of the art and refers to molecular, cellular and interstitial changes in the heart, manifested clinically as changes in size, shape and function of the heart resulting from cardiac load or injury (Cohn J N et al. JACC 2000. 35(3):569-82).

In preferred embodiments of the present invention, the cardiac remodeling is ventricular remodeling, preferably left ventricular remodeling.

Cardiac remodeling to be treated or prevented in accordance with the present invention is pathological (e.g. abnormal or aberrant) cardiac remodeling.

Types of cardiac remodeling suitable for treatment or prevention in accordance with the present invention include myocardial hypertrophy (concentric and eccentric hypertrophy) and ventricular dilation.

Conditions that may lead to (or cause) cardiac remodeling and/or chronic heart failure are conditions that cause increased cardiac load or injury, and therefore for subjects (i.e. patients) having (or suspected of having) such conditions, the treatment or prevention of cardiac remodeling and/or chronic heart failure in accordance with the present invention would be of benefit. Put another way, anti-remodeling therapy, or the reduction of cardiac remodeling, or therapy inhibiting the development of chronic heart failure would be of benefit in such subjects.

Conditions that may lead to cardiac remodeling and/or chronic heart failure include cardiomyopathies, heart valve disease and dysfunction including aortic valve (AV) diseases (such as aortic valve insufficiency, aortic valve regurgitation and aortic stenosis (AV stenosis)), hypertension, pulmonary hypertension, congenital heart disease and coronary artery disease, myocardial infarction, and arrhythmias. For the avoidance of doubt, although the conditions listed in this paragraph, including myocardial infarction, are conditions which may lead to cardiac remodeling and/or chronic heart failure, these conditions are not themselves examples of cardiac remodeling. Acute ischemic injury and reperfusion injury is also not an example of cardiac remodeling. However, as such conditions may lead to (cause) cardiac remodeling and/or chronic heart failure, subjects having, or suspected of having, one or more of these conditions are preferred subjects for treatment (or for the preventative uses) in accordance with the present invention. Particularly preferred are subjects having, or suspected of having, valve diseases. Other particularly preferred subjects are subjects having, or suspected of having, hypertension or valve diseases. Other particularly preferred subjects are subjects having, or suspected of having, aortic valve stenosis. Other particularly preferred subjects are those having, or suspected of having, coronary artery disease and/or myocardial infarction. Also preferred are subjects who have undergone myocardial infarction. Put another way, also preferred are subjects in the chronic phase after myocardial infarction. Acute myocardial infarction is not treated (or prevented) in accordance with the present invention.

Subjects with signs of cardiac remodeling (e.g. myocardial hypertrophy, ventricular dilation) or with overt heart failure, even when the underlying etiology cannot be detected, are also suitable for treatment in accordance with the present invention as preventing further cardiac remodeling or treating existing cardiac remodeling or reducing cardiac remodeling would be beneficial in these subjects.

In some embodiments, subjects with risk factors for cardiac remodeling and heart failure development (e.g. subjects with those conditions that may lead to cardiac remodeling and/or chronic heart failure described herein) are also suitable for treatment (including preventative uses) in accordance with the present invention.

In some embodiments a subject does not have acute ischemic injury and/or reperfusion injury.

Cardiac remodeling can lead to chronic heart failure. As chronic heart failure can be caused by (i.e. result from) cardiac remodeling, heart failure is a preferred disease to be treated or prevented in accordance with the present invention. In a particularly preferred embodiment, the disease to be treated or prevented is chronic heart failure.

Heart failure is a term of the art and refers to a clinical syndrome defined by typical symptoms and signs resulting from any structural or functional abnormality of the heart; where the abnormalities may impair the ability to fill or eject blood, and/or lead to failure to deliver sufficient oxygen to meet the requirements of the metabolizing tissues, despite normal filling pressures, or only at the expense of increased filling pressures (ESC Guidelines for the diagnosis and treatment of acute and chronic heart failure. McMurray J J et al. European Heart Journal 2012, 14(8):803-69; 2013 ACCF/AHA Guideline for the Management of Heart Failure, Yanzy C W et al. Circulation 2013, 128, e240-e327).

Heart failure suitable for treatment or prevention in accordance with the present invention includes chronic heart failure. Chronic heart failure includes congestive heart failure, systolic or contractile dysfunction (e.g. systolic heart failure) or heart failure with reduced ejection fraction, and heart failure in stage A-D (A, B, C, D) according to the American Heart Association staging. Chronic heart failure also includes diastolic heart failure or heart failure with preserved ejection fraction.

The above definitions of heart failure are also often used in the art to define "chronic heart failure". For the avoidance of doubt, "chronic heart failure" does not include "acute" heart failure. Acute heart failure can be defined as a gradual or rapid change in heart failure signs and symptoms resulting in a need for urgent therapy such as inotropes and includes pulmonary edema and cardiogenic shock (Gheorghiade et al, Circulation 2005, 112(25):3958-68).

In preferred embodiments, acute heart failure is not treated.

In accordance with the present invention, the ADAMTS versicanase inhibitors or ADAMTS aggrecanase inhibitors do not treat or prevent cardiac remodeling by treating or preventing one or more conditions that may lead to cardiac remodeling (e.g. the acute phase of myocardial infarction), but rather have an effect (e.g. a direct effect) as drugs to reduce, treat or prevent cardiac remodeling and/or heart failure itself. Thus, inhibitors in accordance with the present invention act to reduce or prevent alterations in the composition and/or structure of the extracellular matrix (e.g. by reducing cleavage of versican or aggrecan). Thus, the present invention is useful for the treatment or prevention of the chronic stages/phases of diseases or conditions. Thus, the present invention is useful for the treatment or prevention of cardiac remodeling or heart failure after the acute stages/phases of diseases or conditions. For example, in some embodiments, the ADAMTS versicanase inhibitors or ADAMTS aggrecanase inhibitors act to reduce cardiac remodeling and/or heart failure in the chronic phase/stage of a disease or condition, e.g. in the chronic phase after myocardial infarction. The ADAMTS versicanase inhibitors or ADAMTS aggrecanase inhibitors may thus be administered to subjects in the chronic phase of a disease or condition or after the acute phase of a disease or condition, for example in the chronic phase after myocardial infarction. In the art, "chronic" generally relates to long duration, typically with stable treated symptoms. In contrast, "acute" typically means rapid onset. The ADAMTS versicanase inhibitors or ADAMTS aggrecanase inhibitors may also be administered to subjects with heart failure in stages A, B, C or D (preferably in stages A, B or C) according to the American Heart Association staging.

In some embodiments, treatment (including preventative uses) with an ADAMTS inhibitor (e.g. ADAMTS4 inhibitor or ADAMTS5 inhibitor) is initiated (the administration of the inhibitor is started) at least 2 days after cardiac injury, e.g. at least 2 days after myocardial infarction. In some embodiments, treatment (including preventative uses) is initiated at least 3 days, at least 4 days, at least 5 days, at least 6 days, at least 7 days, at least 14 days or at least 28 days after cardiac injury (e.g. after myocardial infarction). For example, treatment (including preventative uses) may be initiated 2, 3, 4, 5, 6, 7, 8, 9, 10, 11, 12, 13, 14, 15, 16, 17, 18, 19, 20, 21, 22, 23, 24, 25, 26, 27 or 28 days after cardiac injury (e.g. after myocardial infarction). In some embodiments, treatment (including preventative uses) is initiated 5-15 days after cardiac injury (e.g. after myocardial infarction), e.g. 8-10 days after cardiac injury (e.g. after myocardial infarction).

In some embodiments, the timings discussed in the preceding paragraph are in relation to the time of onset/initiation of myocardial infarction. In some embodiments, the timings discussed in the preceding paragraph are in relation to the time from which the myocardial infarction has stabilized (e.g. the time from which the infarction is no longer increasing in size).

Thus in some embodiments, if a subject has undergone myocardial infarction, treatment (including preventative uses) with an ADAMTS inhibitor (e.g. ADAMTS4 inhibitor or ADAMTS5 inhibitor) may be initiated at one of the time points set out above. In some embodiments, if a subject has undergone myocardial infarction, treatment (including preventative uses) with an ADAMTS inhibitor (e.g. ADAMTS4 inhibitor or ADAMTS5 inhibitor) may be initiated in the chronic phase after myocardial infarction (and not whilst the subject is undergoing myocardial infarction).

In some embodiments, in subjects having undergone myocardial infarction, treatment (including preventative uses) with an ADAMTS inhibitor (e.g. ADAMTS4 inhibitor or ADAMTS5 inhibitor) is initiated (the administration of the inhibitor is started) after complete scarring and thinning of the infarct area. Thus, in some embodiments, infarct size is not affected by the treatments (including preventative uses) of the invention.

Thus, if a subject has undergone myocardial infarction, treatment (including preventative uses) with an ADAMTS inhibitor (e.g. ADAMTS4 inhibitor or ADAMTS5 inhibitor) may be initiated after complete scarring and thinning of the infarct area. Thus, in some embodiments, if a subject has undergone myocardial infarction, infarct size is not affected by the treatments (including preventative uses) of the invention.

In some embodiments, the present invention provides an inhibitor of an ADAMTS proteoglycanase (e.g. an inhibitor of an ADAMTS versicanase and/or of an ADAMTS aggrecanase) as defined above for use in treating or preventing chronic heart failure in a subject.

In one aspect, the present invention provides one or more of the specific compounds described above for use in treating or preventing cardiac remodeling or chronic heart failure in a subject. Embodiments of the uses of the invention described above apply, mutatis mutandis, to this aspect of the invention.

In preferred embodiments of the present invention, the inhibitor is pentosan polysulfate (PPS), the ADAMTS enzyme to be inhibited is an ADAMTS versicanase and the disease to be treated or prevented is heart failure. In particularly preferred embodiments, the inhibitor is pentosan polysulfate (PPS), the ADAMTS versicanase is the ADAMTS4 enzyme and the disease to be treated or prevented is chronic heart failure. In another preferred embodiment, the inhibitor is pentosan polysulfate (PPS), the ADAMTS versicanase is the ADAMTS5 enzyme and the disease to be treated or prevented is chronic heart failure.

Alternatively viewed, the invention provides an inhibitor of an ADAMTS proteoglycanase enzyme (e.g. an inhibitor of an ADAMTS versicanase and/or of an ADAMTS aggrecanase) as described elsewhere herein for use in reducing cardiac remodeling. Preferably, the reduction is a clinically significant reduction.

Alternatively viewed, the present invention provides a method of treating or preventing cardiac remodeling or treating or preventing heart failure which method comprises administering to a subject in need thereof a therapeutically effective amount of an inhibitor of an ADAMTS proteoglycanase (e.g. an inhibitor of an ADAMTS versicanase and/or of an ADAMTS aggrecanase). Embodiments of the uses of the invention described above apply, mutatis mutandis, to this aspect of the invention. A therapeutically effective amount can be determined based on the clinical assessment and can be readily monitored.

In one embodiment, the present invention provides a method of treating or preventing cardiac remodeling or treating or preventing heart failure which method comprises administering to a subject in need thereof a therapeutically effective amount of an inhibitor of ADAMTS4 or ADAMTS5, wherein said subject is a subject with cardiac remodeling or with chronic heart failure, or with a condition that may lead to cardiac remodeling and/or chronic heart failure. In some embodiments, the inhibitor inhibits both ADAMTS4 and ADAMTS5.

Further alternatively viewed, the present invention provides the use of an inhibitor of an ADAMTS proteoglycanase (e.g. an inhibitor of an ADAMTS versicanase and/or of an ADAMTS aggrecanase) in the manufacture of a medicament for treating or preventing cardiac remodeling or treating or preventing heart failure. Embodiments of the uses of the invention described above apply, mutatis mutandis, to this aspect of the invention.

In one embodiment, the present invention provides the use of an inhibitor of ADAMTS4 or ADAMTS5 in the manufacture of a medicament for treating or preventing cardiac remodeling in a subject or treating or preventing heart failure in a subject, wherein said subject is a subject with cardiac remodeling or with chronic heart failure, or with a condition that may lead to cardiac remodeling and/or chronic heart failure.

The embodiments and explanations of the uses and methods of the present invention as described above in relation to ADAMTS versicanases and/or ADAMTS aggrecanases also apply, mutatis mutandis, to the present invention in so far as it relates to ADAMTS proteoglycanases in general.

Treatments (or preventative therapies) in accordance with the present invention may involve co-administration with another agent that is used in the treatment or prevention of heart disease, e.g. another anti-remodeling agent or another agent for the treatment of heart failure. In one embodiment, the further agent for co-administration is an inhibitor of the sympathetic or RAA (renin-angiotensin-aldosteron) systems. In one embodiment, the further agent for co-administration is an antagonist of the β-adrenergic receptor or inhibitor of the RAA system.

Subjects in accordance with the present invention will preferably be humans but veterinary treatments (e.g. for cows, sheep, pigs, dogs, cats, horses) are also contemplated. In one embodiment, the subjects in accordance with the present invention are subjects having cardiac remodeling or heart failure. In some embodiments, the subjects are suspected of having cardiac remodeling or heart failure. Subjects in accordance with the present invention may be at risk of developing cardiac remodeling or heart failure.

The inhibitors for use in the present invention may be included in formulations. Such formulations may be for pharmaceutical or veterinary use. Suitable diluents, excipients and carriers for use in such formulations are known to the skilled man.

The compositions (formulations) may be presented, for example, in a form suitable for oral, nasal, parenteral, intravenal, topical or rectal administration, preferably in a form suitable for oral administration.

The active compounds (inhibitors) defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers, either with an aerosol propellant or provided with means for manual compression.

The pharmaceutical compositions (formulations) may be administered parenterally. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the active compound in the form of a nasal or pulmonal spray. As a still further option, the active compound can also be administered transdermally, e.g. from a patch, optionally a iontophoretic patch, or transmucosally, e.g. bucally. Preferably, the active compound is administered orally.

Dosages may vary based on parameters such as the age, weight and sex of the subject. Appropriate dosages can be readily established. By way of example, a dosage of approximately 300 mg/day p.o. may be used (for example for PPS). Appropriate dosage units can readily be prepared.

The pharmaceutical compositions may additionally comprise further active ingredients as described above in the context of co-administration regimens.

In a further aspect, the present invention provides kits comprising one or more of the ADAMTS proteoglycanase inhibitors (e.g. ADAMTS versicanase inhibitors and/or ADAMTS aggrecanase inhibitors), or formulations as defined above for use according to the invention. The kits may comprise further components. Each component may be provided in a separate compartment or vessel. Where convenient and practical, mixtures of components could be provided. The components may be provided in dry, e.g. crystallised, freeze dried or lyophilised, form or in solution, typically such liquid compositions will be aqueous and buffered with a standard buffer such as Tris, HEPES, etc.

The kits may also be provided with instructions for using the kit in accordance with the invention or with directions for how such instructions may be obtained.

The invention will be further described with reference to the following non-limiting Examples with reference to the following drawings in which:

FIG. 1. Elevated mRNA levels of ADAMTS1, -4 and -8 in rats with heart failure after aortic banding Myocardial mRNA expression of ADAMTS versicanases and aggrecanases in rats with (n=6) and without heart failure (n=10) six weeks after AB, normalized to reference gene ribosomal protein L4 (RPL4) and relative to sham (n=9). Box-plots show median (horizontal line), interquartile range (box), 1.5×interquartile range or maximum/minimum range (whiskers) and outliers (o) (>1.5×interquartile range). *p<0.05. HF, heart failure; HT, hypertrophy; AB, aortic banding.

FIG. 2. Elevated mRNA levels of versican and aggrecan in rats after aortic banding Myocardial mRNA expression of versican and aggrecan in rats with (n=6) and without heart failure (n=10) six weeks after aortic banding, normalized to the reference gene ribosomal protein L4 (RPL4) and relative to sham (n=9). Box-plots show median (horizontal line), interquartile range (box), 1.5×interquartile range or maximum/minimum range (whiskers) and outliers (o) (>1.5×interquartile range). *p<0.05. HF, heart failure; HT, hypertrophy; AB, aortic banding.

Figure 3:
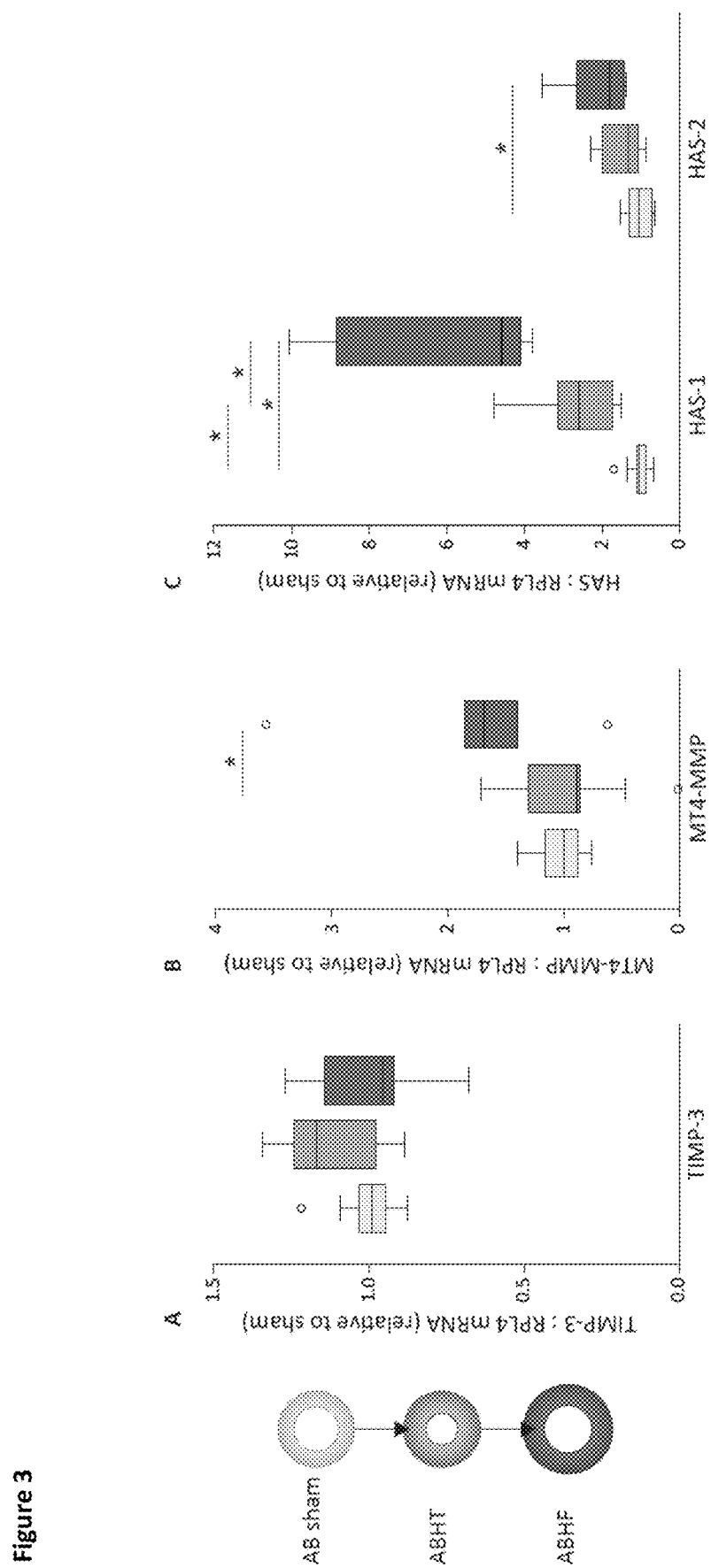

FIG. 3. TIMP-3, HAS and MT4-MMP mRNA levels in rats after aortic banding

Myocardial mRNA expression of TIMP-3, HAS and MT4-MMP in rats with (n=6) and without heart failure (n=10) six weeks after AB, normalized to the reference gene ribosomal protein L4 (RPL4) and relative to sham (n=9). Box-plots show median (horizontal line), interquartile range (box), 1.5×interquartile range or maximum/minimum range (whiskers) and outliers (o) (>1.5×interquartile range). *p<0.05. HF, heart failure; HT, hypertrophy; HAS, hyaluronic acid synthase; MT, membrane-type; AB, aortic banding.

Figure 4:
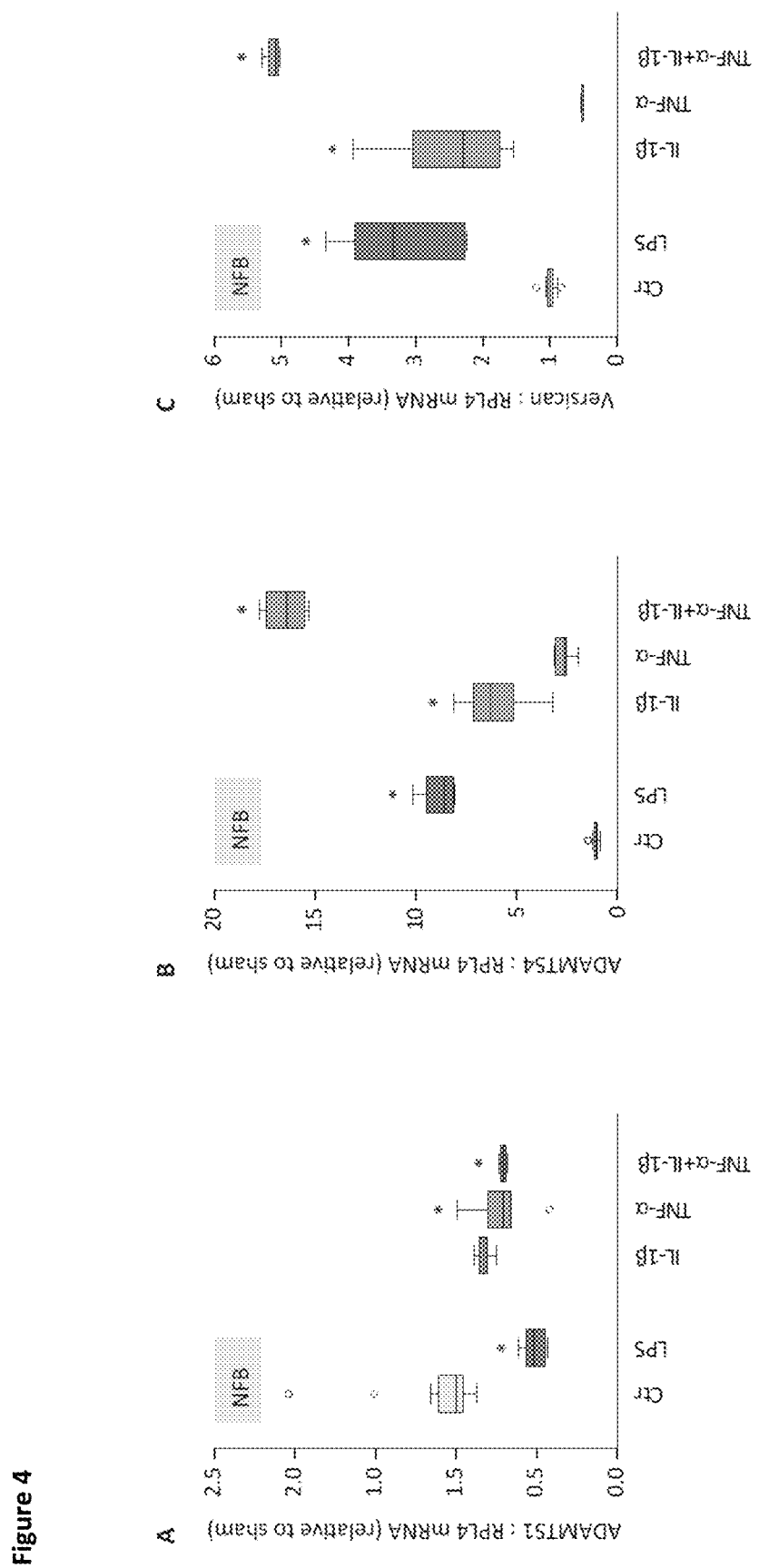
Figure 4:
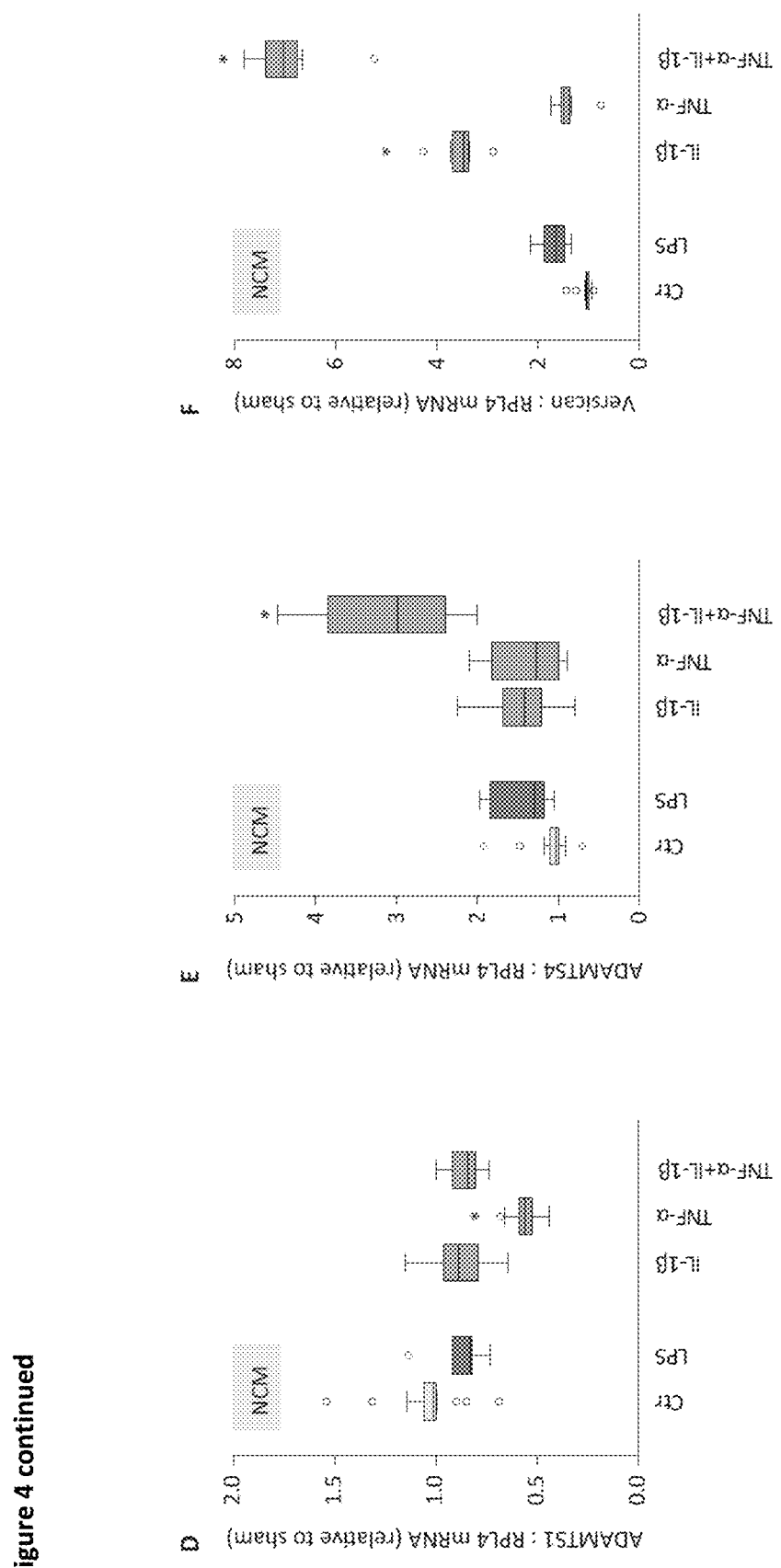

FIG. 4. ADAMTS4 and versican mRNA expression in cardiac fibroblasts and cardiomyocytes is induced by inflammatory mediators mRNA expression in NFB and NCM of ADAMTS1 (A,D), ADAMTS4 (B,E), and versican (C,F) after stimulation with LPS (n=6), IL-1β (n=7), TNF-α (n=10 (NCM)/6 (NFB)), separate and combined (n=7 (NCM)/4 (NFB)). Untreated cells served as control (n=15 (NCM)/18 (NFB)). Box-plots show median (horizontal line), interquartile range (box), 1.5×interquartile range or maximum/minimum range (whiskers) and outliers (o) (>1.5×interquartile range). *p<0.05, compared to control. NFB, neonatal fibroblasts; NCM, neonatal cardiomyocytes.

Figure 5:
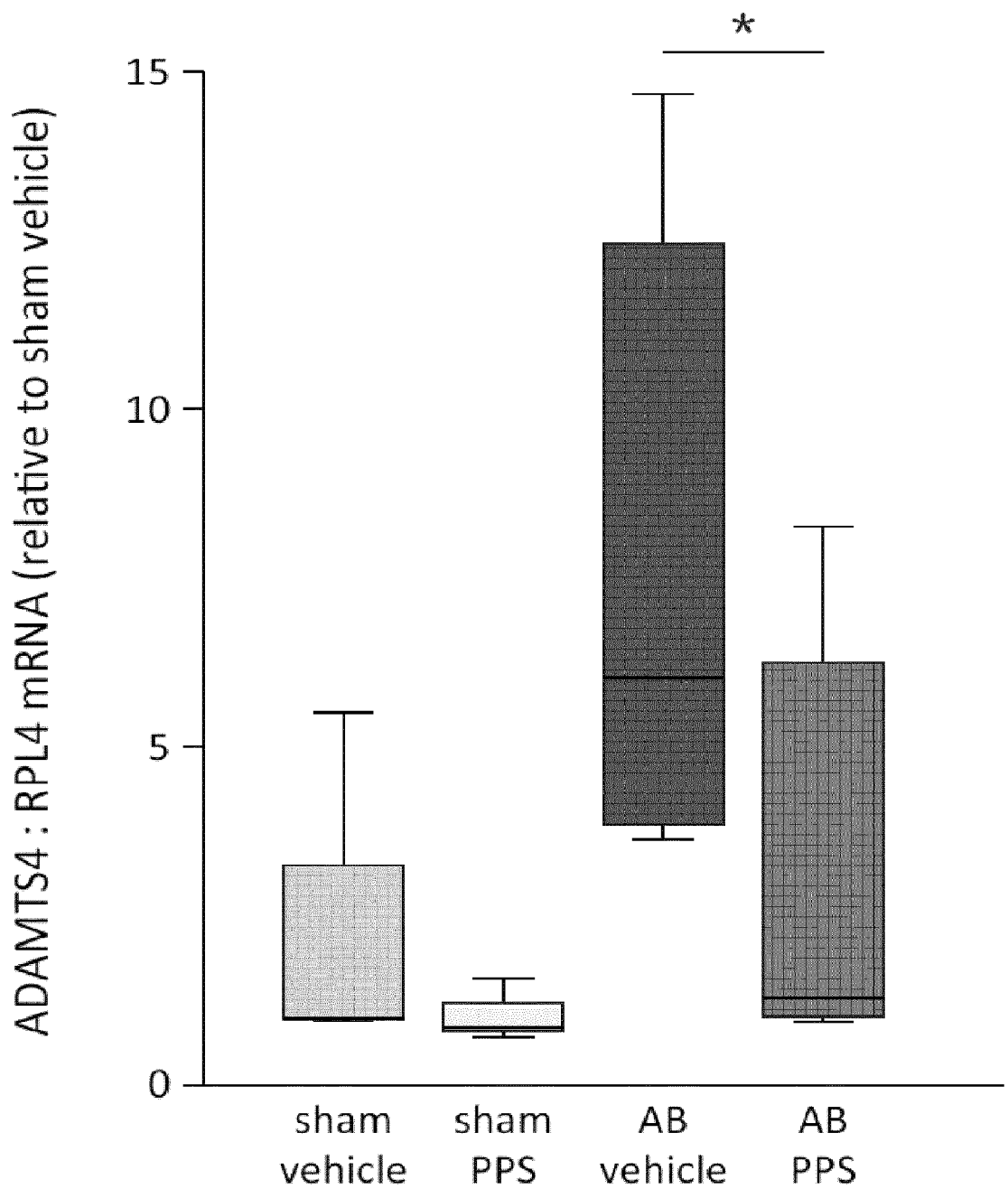

FIG. 5. Decreased ADAMTS4 mRNA level after PPS-treatment

Myocardial mRNA expression of ADAMTS4 in rats treated with PPS (n=10) and vehicle (n=7) six weeks after AB, and sham-operated rats treated with PPS (n=3) normalized to the reference gene ribosomal protein L4 (RPL4) and relative to vehicle-treated sham (n=3). Box-plots show median (horizontal line), interquartile range (box), 1.5× interquartile range or maximum/minimum range (whiskers) and outliers (o) (>1.5×interquartile range). *p<0.05. HF, heart failure; AB, aortic banding.

Figure 6:
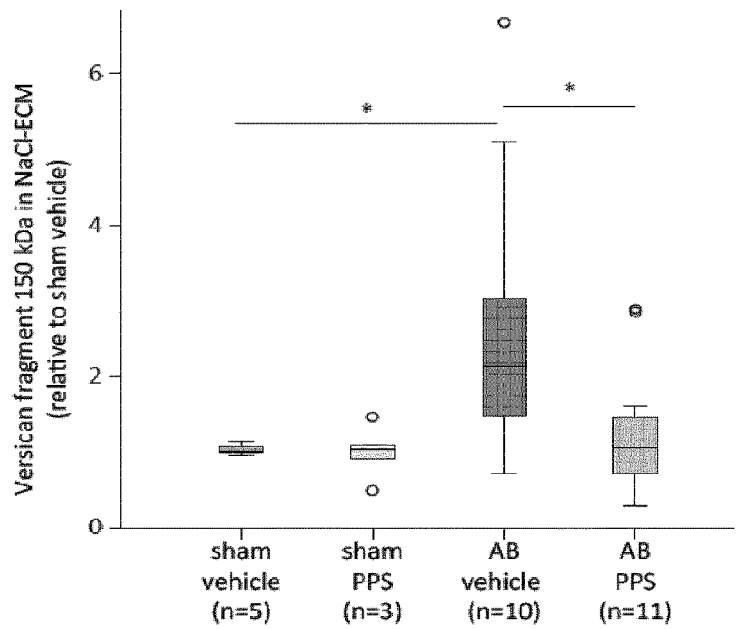
Figure 6:
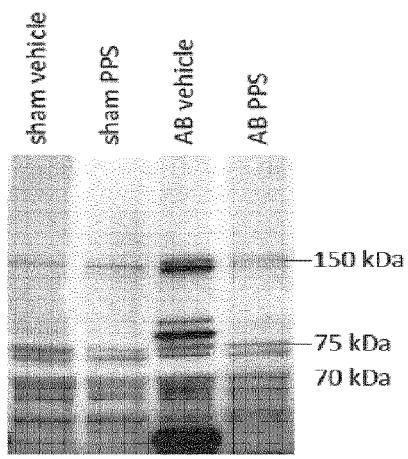
Figure 6:
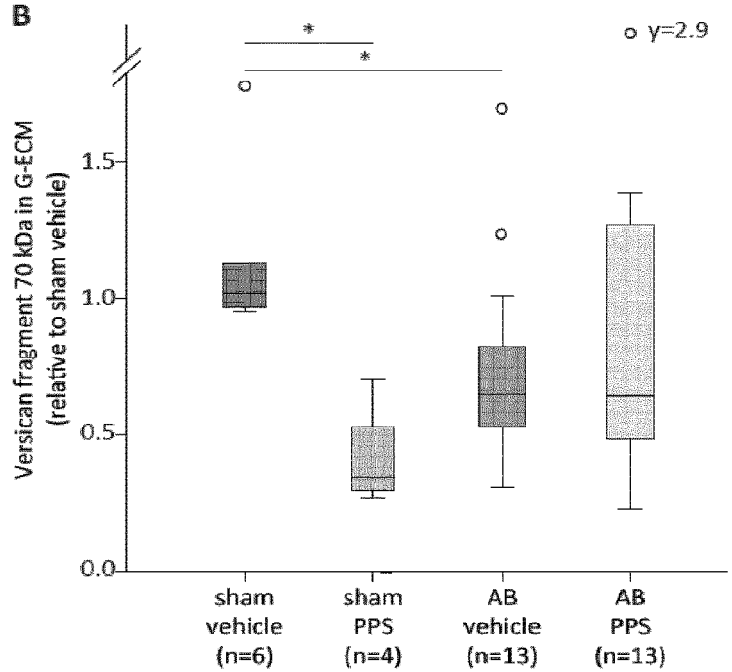
Figure 6:
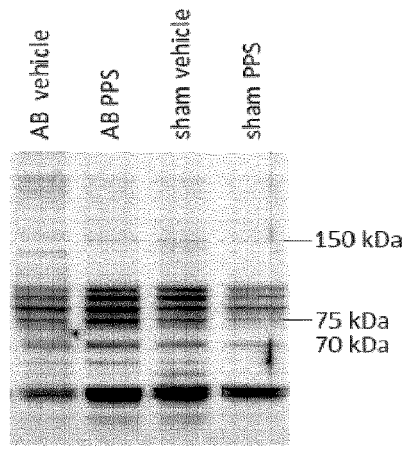
Figure 6:
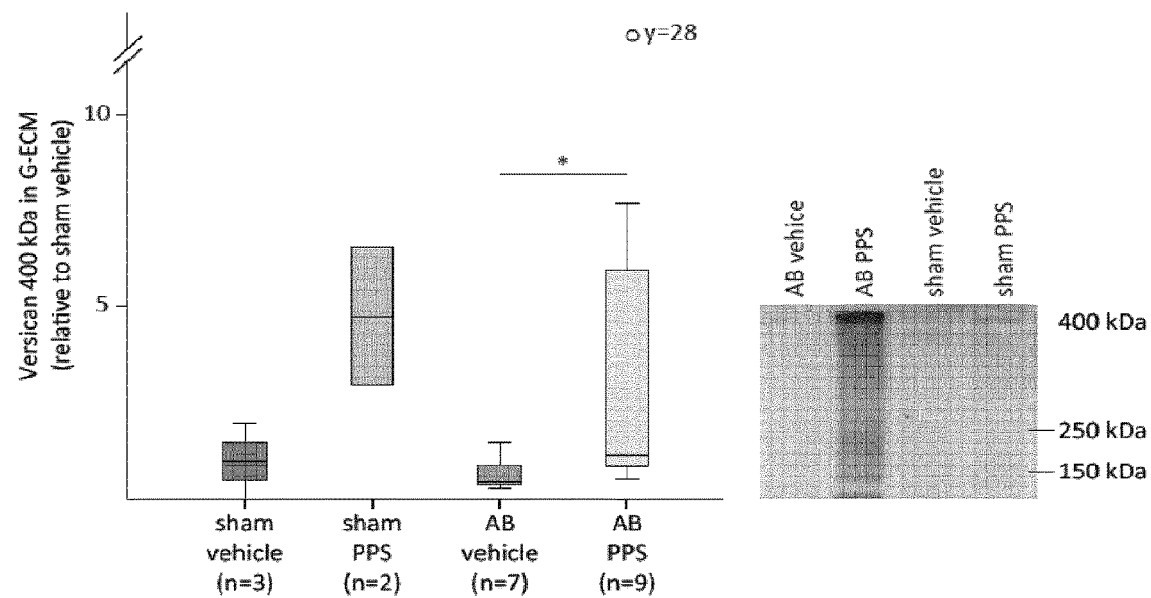
Figure 6:
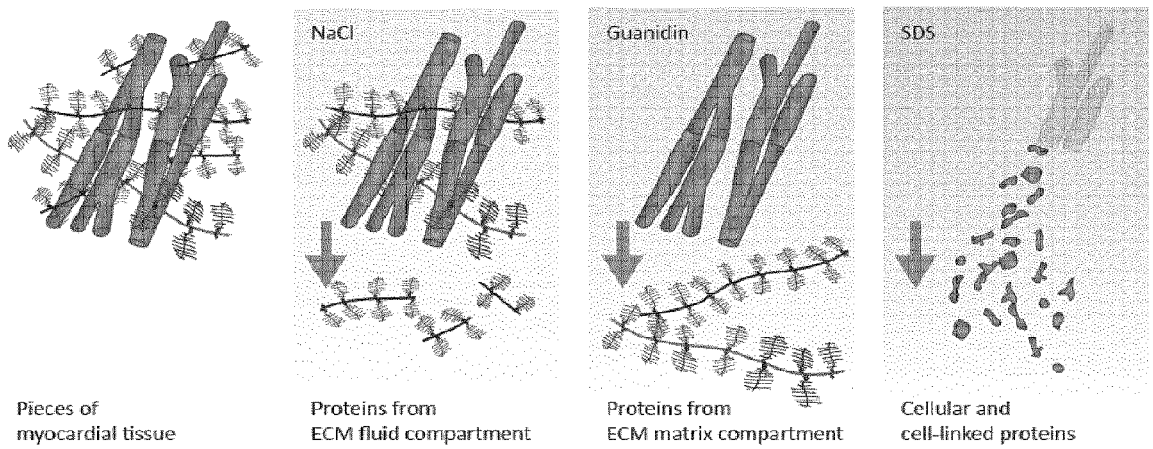
Figure 6:
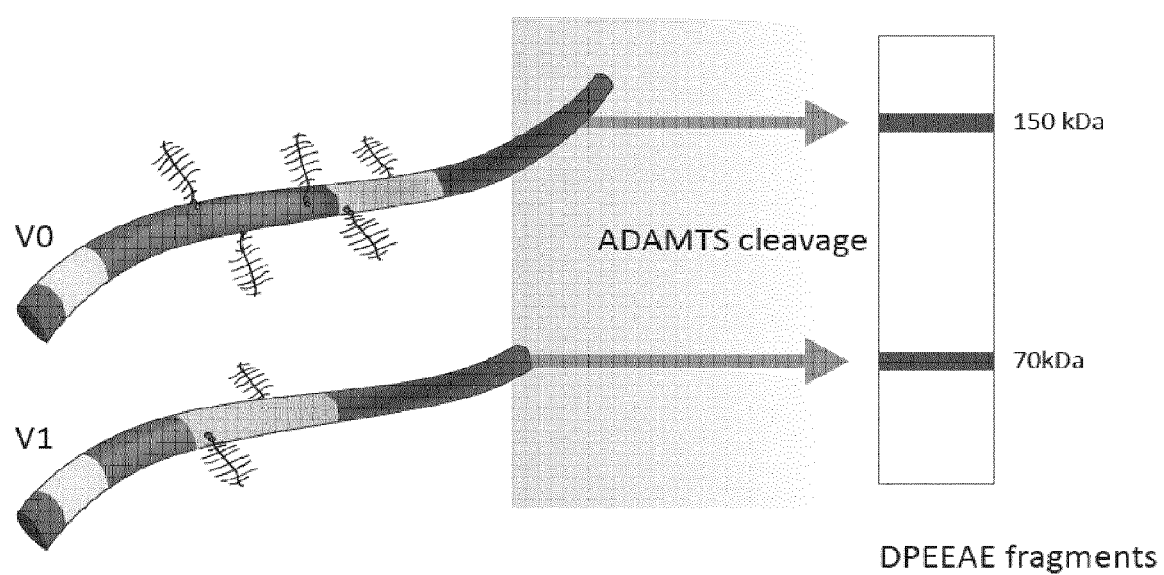

FIG. 6. Versican fragments and full-length protein in AB-rats treated with PPS

Level of p150 versican DPEEAE fragment in NaCl-soluble ECM (A), p70 DPEEAE versican fragment in G-soluble ECM (B), and full-length versican in G-soluble ECM (C), in AB-rats treated with PPS or vehicle. Box-plots show median (horizontal line), interquartile range (box), 1.5×interquartile range or maximum/minimum range (whiskers) and outliers (o) (>1.5×interquartile range). *p<0.05. HF, heart failure; AB, aortic banding, PPS, pentosan polysulfate, G, guanidine.

Figure 7:
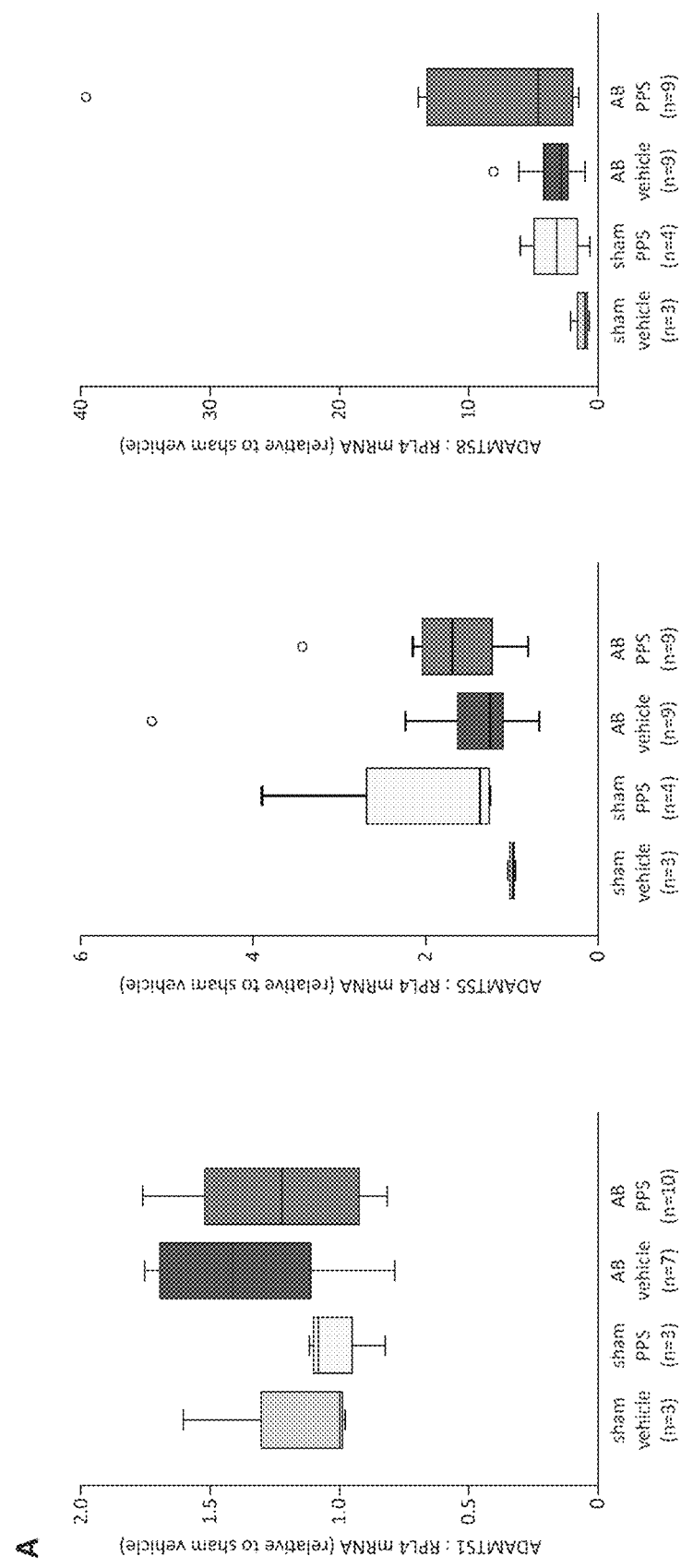
Figure 7:
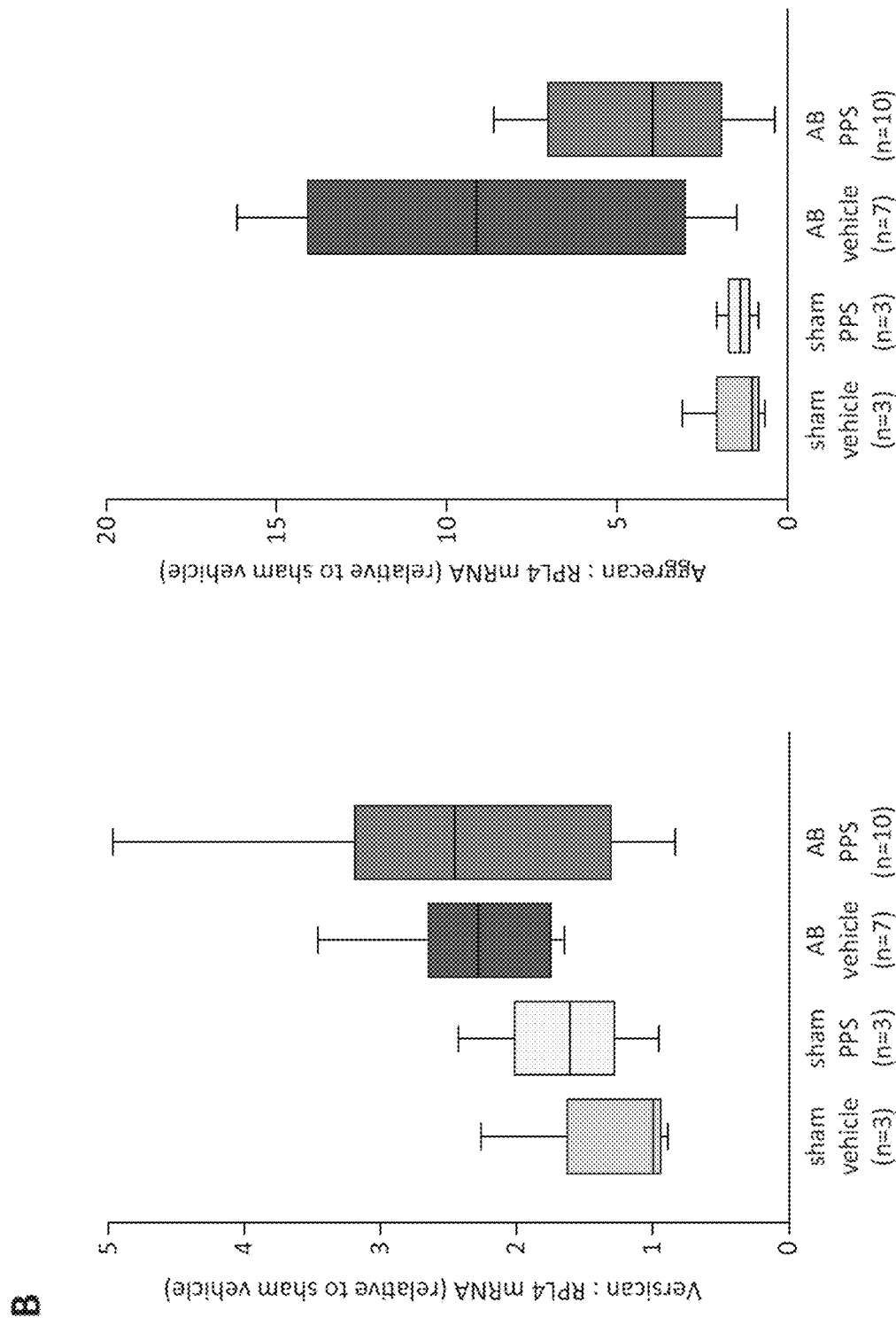
Figure 7:
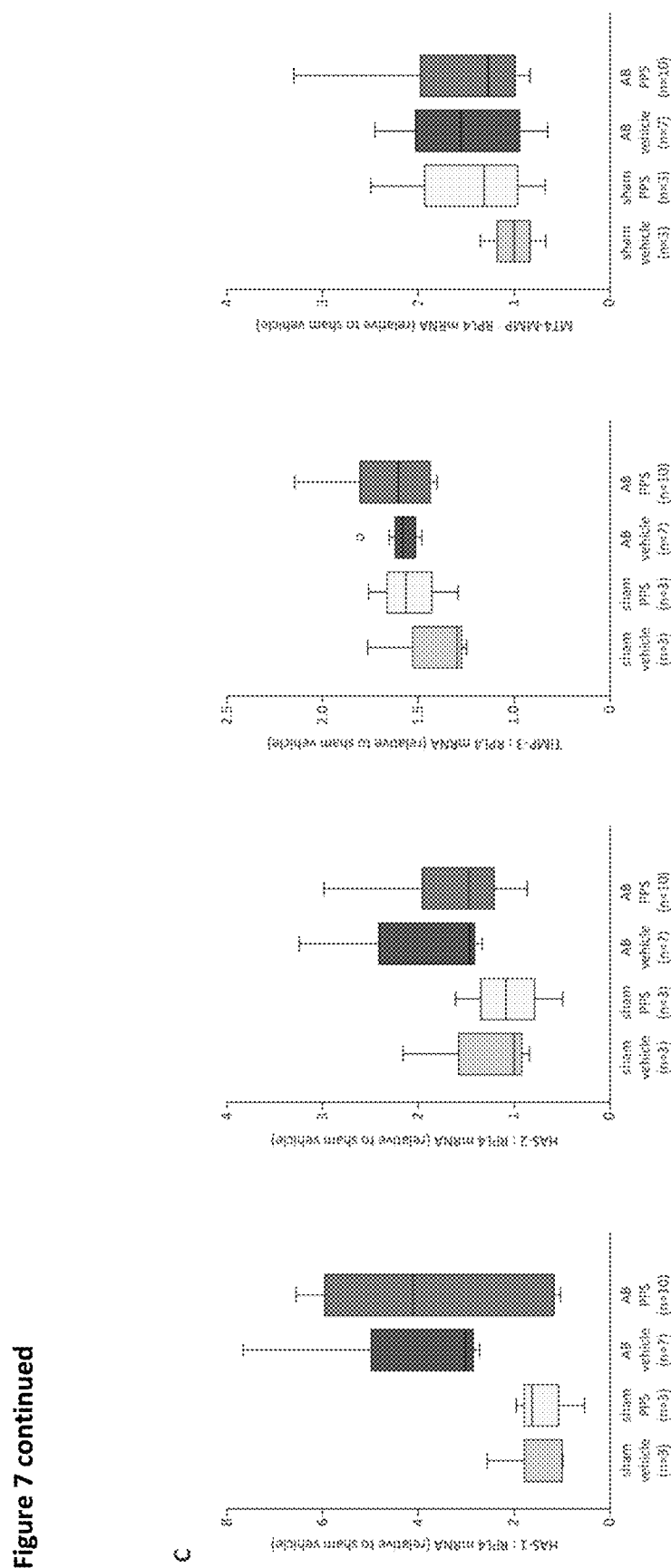
Figure 8:
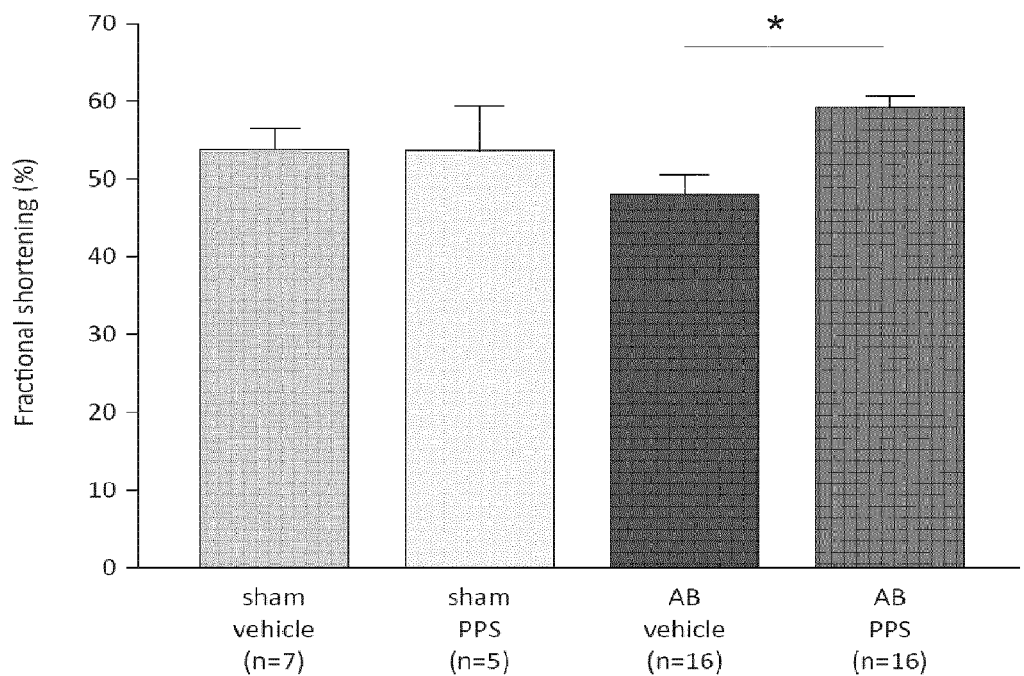
Figure 8:
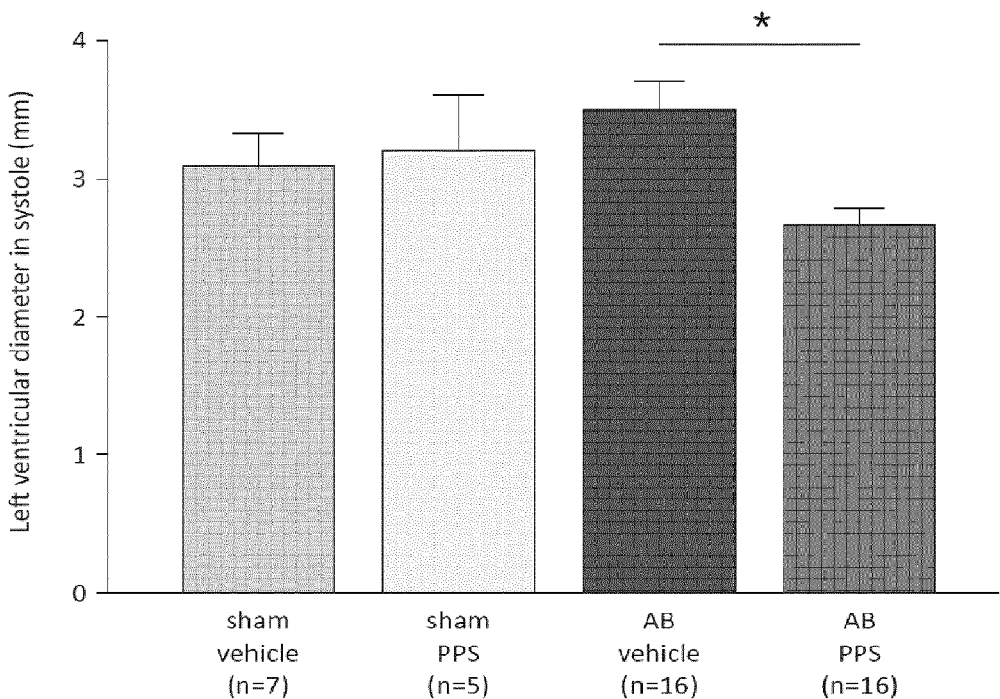
Figure 8:
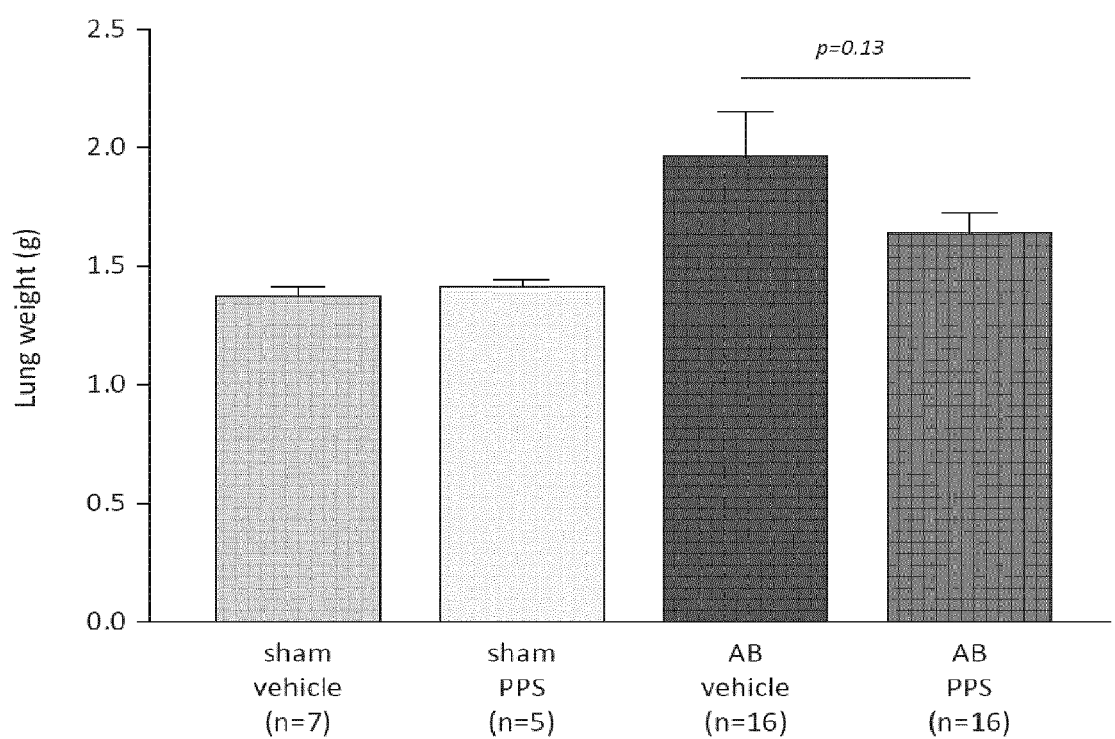

FIG. 7. mRNA levels after pentosan polysulfate treatment in rats after aortic banding Myocardial mRNA expression of ADAMTS1, -5, -8 (A), versican, aggrecan (B), HAS-1, -2, TIMP-3, and MT4-MMP (C) in rats treated with PPS (n=9 or 10) or vehicle (n=7 or 9) six weeks after AB, and sham-operated rats treated with PPS (n=3 or 4) normalized to the reference gene ribosomal protein L4 (RPL4) and relative to vehicle-treated sham (n=3). The bars represent median levels and the error bars the $75^{th}$ percentile. *p<0.05. AB, aortic banding; HF, heart failure, HA, hyaluronic acid;

FIG. 8. Improved systolic function after PPS-treatment in AB-rats

Fractional shortening (A), left ventricular diameter in systole (B), and lung weight (C) in sham and aortic banding rats treated with pentosan polysulfate or vehicle. AB, aortic banding. *p≤0.05.

Figure 9:
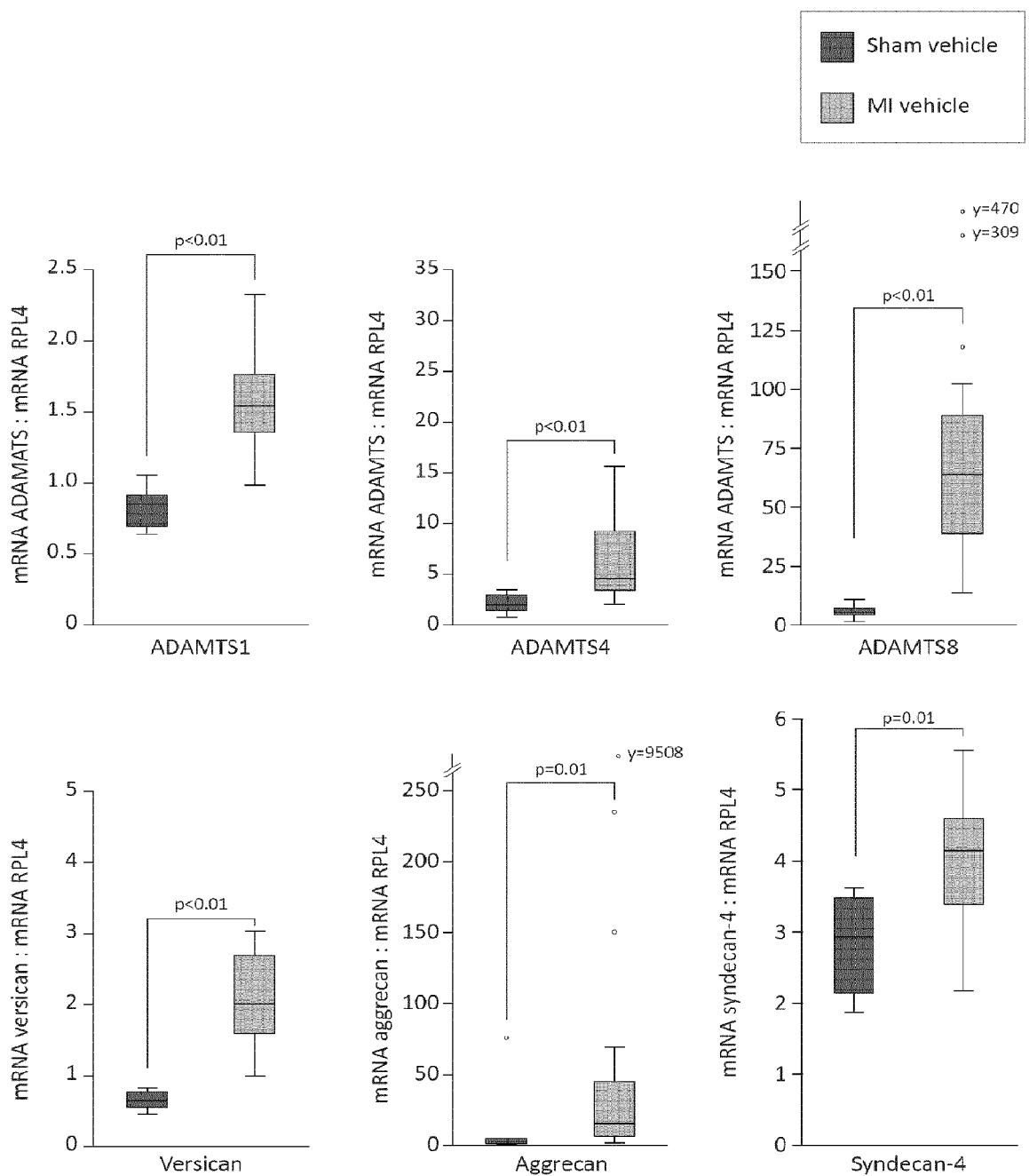

FIG. 9. Increased mRNA expression of ADAMTS and proteoglycans after myocardial infarction mRNA levels of ADAMTS and proteoglycans in vehicle-treated sham (n=6) and vehicle-treated MI rats (n=15). Box-plots show median (horizontal line), interquartile range (box), 1.5×interquartile range or maximum/minimum range (whiskers) and outliers (>1.5×interquartile range). MI, myocardial infarction.

Figure 10:
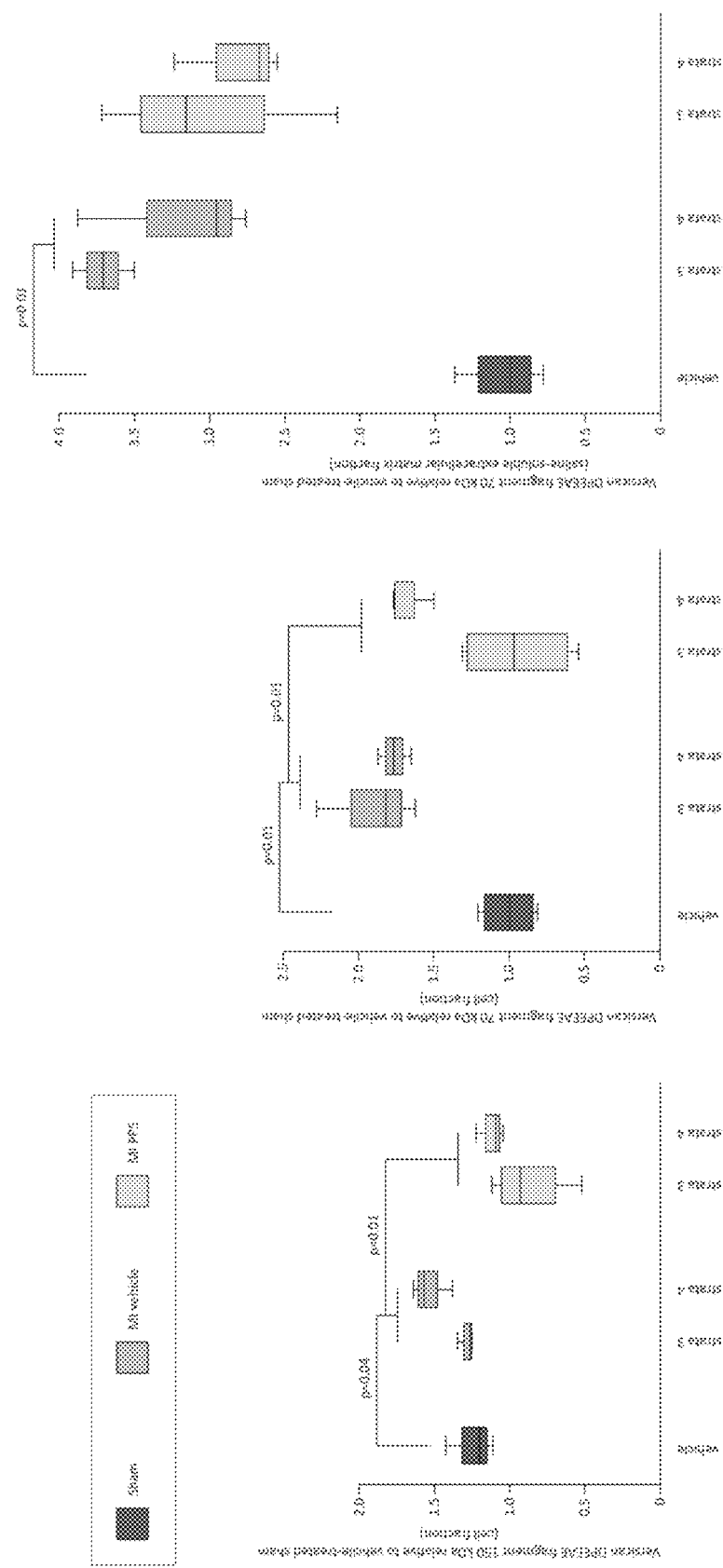
Figure 10:
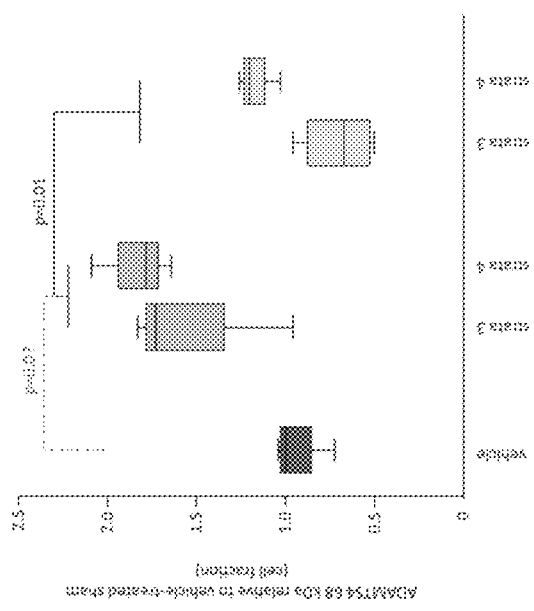
Figure 10:
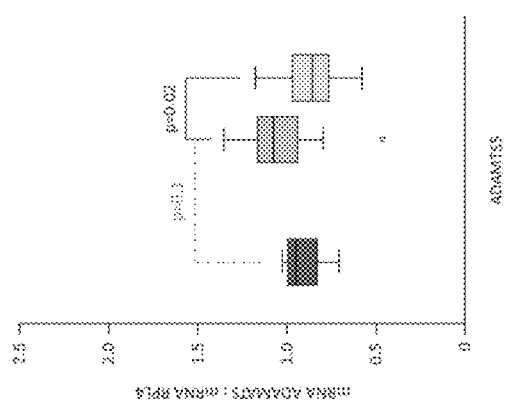
Figure 10:
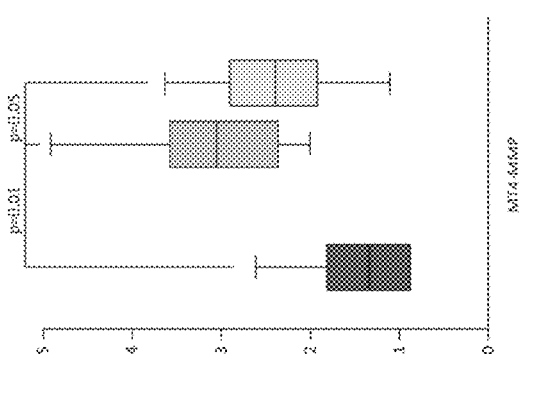

FIG. 10. Reduced levels of ADAMTS4, ADAMTS-induced versican fragments, ADAMTS5 and MT4-MMP after PPS-treatment Protein levels of versican DPEEAE fragments and ADAMTS4 68 kDa form in vehicle-treated sham (n=4), vehicle-treated MI rats in stratum 3 (n=3) and 4 (n=3), and PPS-treated MI rats in stratum 3 (n=4) and 4 (n=3). mRNA levels of ADAMTS5 and MT4-MMP in vehicle-treated sham (n=6), vehicle-treated MI rats (n=15), and PPS-treated MI rats (n=15). Box-plots show median (horizontal line), interquartile range (box), 1.5×interquartile range or maximum/minimum range (whiskers) and outliers (>1.5×interquartile range). MI, myocardial infarction; PPS, pentosan polysulfate.

Figure 11:
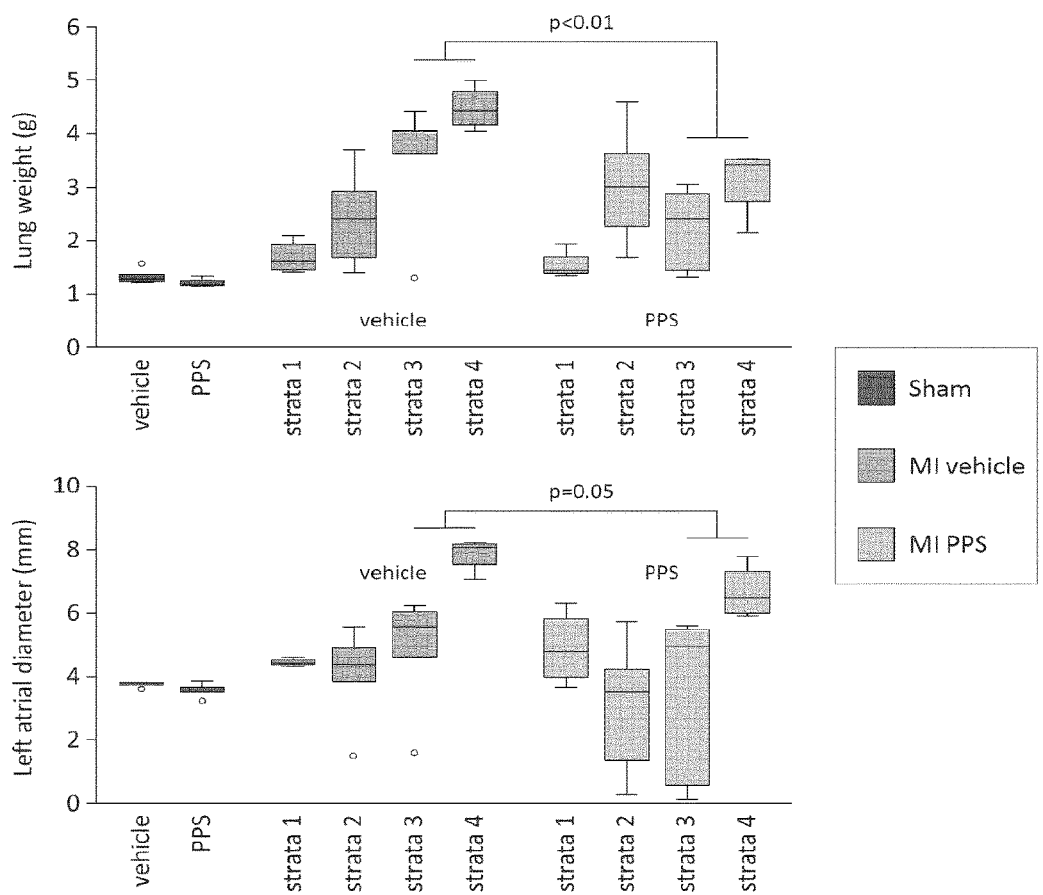

FIG. 11. Reduced heart failure development in PPS-treated rats with large myocardial infarcts Lung weight and left atrial diameter in vehicle-treated sham (n=6), PPS-treated sham (n=6), vehicle-treated MI rats in stratum 1 (n=4), 2 (n=7), 3 (n=5), and 4 (n=4), and PPS-treated MI rats in stratum 1 (n=4), 2 (n=7), 3 (n=6), and 4 (n=5). Box-plots show median (horizontal line), interquartile range (box), 1.5×interquartile range or maximum/minimum range (whiskers) and outliers (>1.5×interquartile range). MI, myocardial infarction; PPS, pentosan polysulfate.

EXAMPLE 1

Introduction

We hypothesized that alterations in versicanase and aggrecanase activity of ADAMTS (a disintegrin and metalloprotease with thrombospondin motifs) proteases in the extracellular matrix (ECM) contributes to heart failure development, thus representing a potential therapeutic target in heart failure. In the first part of the study, myocardial levels of versican, aggrecan, and their cleaving ADAMTS proteases were examined in rats exposed to aortic banding (AB), divided into two groups with hypertrophy (ABHT) or heart failure (ABHF), while versican and selected ADAMTS proteases were further analysed in neonatal cardiomyocytes (NCM) and cardiac fibroblasts (NFB) after treatment with inflammatory mediators. Based on the initial findings, a promising target among the ADAMTS proteases has been identified, and in the second part of the study, we evaluated in AB-rats the effect of in vivo inhibition of this target by treatment with pentosan polysulfate (PPS) on heart function, versican expression level and fragmentation.

Methods

Aortic Banding Rat Model

The experimental procedures conformed to the *European Convention for the Protection of Vertebrate Animals Used for Experimental and Other Scientific Purposes*, and the protocols were approved by the Norwegian Council for Animal Research. Male Wistar rats weighing 160-170 g underwent AB essentially as described previously (Lunde et al. Physiol Genomics 2011. 44(2):162-72). Briefly, the ascending aorta was dissected free through a right hemithoracotomy, and ligated (3-0 silk) against a steel wire. The sham-operated rats (sham) were subjected to the same surgical procedure with a loose suture around the aorta. In all surgical procedures performed, a mixture of 67% $N_2O$, 28% $O_2$, and 4% isoflurane in an anaesthesia chamber was used for preoperative sedation. To maintain anaesthesia peroperatively, a mixture of 69% $N_2O$, 29% $O_2$, and 2% isoflurane was given by the endotracheal tube and the animals were ventilated on a respirator (Zoovent, Triumph Technical Services, Milton Keynes, UK). Buprenorphine was given as postoperative analgesia after AB.

Animal Phenotyping and Tissue Sampling

In vivo heart function was evaluated using the Vevo2100 system (Visualsonics Inc, Canada) as previously described (Sjaastad et al. J Appl Physiol 2000; 89:1445-54). Thereafter, the heart was excised under deep anaesthesia, washed in saline and blotted dry to remove blood in the cardiac chambers. The heart chambers were separated by rapid dissection, before being snap-frozen in liquid nitrogen and stored at −70° C. until further analyses. For AB rats not receiving PPS- or vehicle treatment, selection into heart failure (ABHF) or hypertrophy (ABHT) groups was based on echocardiographic and postmortem analysis, as follows: Inclusion criteria for ABHF group were increased lung weight (>2.5 g), increased posterior wall diameter in diastole (PWDd) (>2.0 mm) and increased left atrial diameter (>5.0 mm), while criteria for inclusion in the ABHT group were increased PWDd (>2.0 mm), increased left ventricular weight (>0.75 g) and preserved lung weight (<2.0 g).

Isolation of Neonatal Cardiomyocytes and Fibroblasts

Primary rat NCM and NFB were isolated from 1-3 day old Wistar rats (Taconic, Skensved, Denmark) as previously described (Strand M E et al. FEBS Journal 2013. 280(10): 2228-47). Briefly, hearts were removed and the left ventricle dissected and digested using collagenase, and cell suspension was transferred to uncoated culture flasks allowing NFB to attach, while NCM were transferred to gelatin-coated culture dishes (Corning international, Corning, N.Y.) in plating medium [Dulbecco's Modified Eagles Medium (Sigma) supplemented with penicillin/streptomycin (Sigma), 44 mmol $l^{-1}$ NaHCO, medium 199 (Sigma), 26 mmol $l^{-1}$ NaHCO3, horse serum (14-703E, Bio-Whittaker, Walkersville, ML) and fetal calf serum (14-701E, Bio-Whittaker)]. The cells were maintained in serum-free medium (plating medium without serum) 24 hours before treatment with inflammatory mediators.

Thereafter, NCM and NFB were treated with 10 ng/ml IL-1β (501-RL-010, R&D Systems, Minneapolis, Minn.) and 50 ng/ml TNF-α (PMC3014, BioSource International, Camarillo, Calif.) separately and combined, and 1000 ng/ml LPS (201, List laboratories, Campbell, Calif.) for 24h.

In Vivo Inhibition of ADAMTS4

Three days after AB, rats were stratified by the gradient over the stenosis to ensure similar degree of cardiac stress. Two and two stratified rats were randomized to either 6 mg/kg of the sulfated polysaccharide sodium pentosan polysulfate (PPS) (Interfarm AS, Norway) or vehicle (0.9%

NaCl) injected subcutaneously every third day. Rats were observed at daily basis, and no side effects including haemorrhage were observed. Six weeks after AB or sham operation, the rats were examined by echocardiography and postmortem analysis, performed by experienced investigators (IS, JMA) blinded to treatment group.

RNA Isolation, Reverse Transcription and Quantitative Real Time PCR

The mRNA levels of ADAMTS1, -4, -5, and -20 possessing versicanase and/or aggrecanase activity, ADAMTS8, -9, -15, -16, and -18 possessing aggrecanase activity, and ADAMTS6 (for which the substrate is yet to be determined) (Shiomi et al. Pathology International 2010. 60(7):477-96) were quantified in rat left ventricle by quantitative real time (qRT)-PCR, and ADAMTS demonstrating altered mRNA levels after AB were also quantified after PPS-treatment. In addition, mRNA levels of proteins known to modulate ADAMTS activity or versican function were measured; tissue inhibitor of metalloprotease (TIMP)-3, hyaluronic acid (HA) synthase 1 and 2, and membrane-type (MT)4-MMP, while mRNA levels of ADAMTS1, -4, and versican were quantified in NFB and NCM.

Total RNA was isolated from the left ventricle in AB rats, neonatal rat cardiomyocytes and fibroblasts (RNeasy mini kit, Qiagen, Valencia, Calif.). All RNA samples were quality assessed, and RNA integrity numbers (RIN)>7.5 (Agilent Bioanalyzer, Agilent Technologies, Palo Alto, Calif., USA) and a 280/260 ratio >2 (Nanodrop ND-1000 Spectrophotometer (Thermo Scientific) were accepted. Reverse transcription reactions were performed with iScript Select cDNA Synthesis Kit (Bio-Rad Laboratories, Inc., Hercules, Calif.). Pre-designed TaqMan assays (Applied Biosystems, Foster City, Calif.) were used in quantitative real-time polymerase chain reaction (qPCR) to determine gene expression of ADAMTS1 (Rn01646120_g1), ADAMTS4 (Rn02103282_s1), ADAMTS5 (Rn01458486_m1), ADAMTS6 (Rn01489864_m1), ADAMTS8 (Rn01524921_m1), ADAMTS9 (Rn01425216_m1), ADAMTS15 (Rn01524703_m1), ADAMTS16 (Rn01537448_m1), ADAMTS18 (Rn01426916_m1), ADAMTS20 (Rn01407540_m1), versican (Rn01493755_m1), aggrecan (Rn00573424_m1), HAS-1 (Rn01455687_g1), HAS-2 (Rn00565774_m1), TIMP-3 (Rn00441826_m1) and MT4-MMP (Mm00449292_m1). For normalization, the reference gene ribosomal protein L4 (RPL4) (Rn008211091_g1) was used. The results were detected on an ABI PRISM 7900 Sequence Detection System (Applied Biosystems, CA).

Fractional Protein Isolation of Rat Left Ventricle

Proteins from rat myocardium were extracted as previously described (Didangelos et al. J Biol Chem 2012. 287(23):19341-5). Briefly, proteins were separated into three fractions; NaCl-soluble extracellular proteins (NaCl-ECM) and guanidine-soluble extracellular proteins (G-ECM), containing the fluid and matrix compartment of ECM respectively, in addition to cellular and cell-linked proteins dissolvable in SDS (SDS-samples) (FIG. 6D). NaCl-ECM and G-ECM were deglycosylated to remove GAG chains using 4 mU/NaCl-sample and 12 mU/G-sample of Chondroitinase ABC (from *Proteus vulgaris*, G3667, Sigma-Aldrich, MO) and 5 mU/NaCl-sample and 15 mU/G-sample of keratanase (endo-β-galactosidase from *Bacteroides fragilis*, G6920, Sigma-Aldrich), as previously described (Didangelos A et al. supra).

Immunoblotting

Protein concentrations were measured using the Micro BCA Protein Assay Kit (Pierce/Thermo Scientific, IL). Sample buffer was mixed with 5-25 µg (G-samples) or 30 µg (NaCl and SDS samples) of the protein lysate, denatured at 96° C. for 10 min, and run on 1.5 mm 4-12% Bis-Tris gradient gels (Nupage, Invitrogen, CA), with MOPS SDS running buffer until the 37 kDa protein marker reached the bottom of the gel. All protein extracts were loaded blinded to group.

SDS-PAGE and immunoblotting was performed as described in the Criterion BioRad protocol, using polyvinylidene fluoride (PVDF) membranes (GE Healthcare Life Sciences, Uppsala, Sweden). Blots were developed using the ECL Plus Western Blotting Detection System (GE Healthcare) and visualized in the Las-4000 mini from Fujifilm (Japan). Before reprobing, stripping was performed using the Restore Western Blot Stripping Buffer (21059, Thermo Scientific, IL).

Since two of the protein fractions contained extracellular proteins, Coomassie staining of the blots was chosen to control for equal loading. Equal loading was observed for SDS and NaCl protein fraction samples. For G-fractions Coomassie staining revealed signs of potential unequal loading and the protein levels in G samples were therefore normalized to the 65 kDa band in the corresponding Coomassie stained blot.

Antibodies

Membranes were blocked in 5% non-fat dry-milk (170-6404, BioRad) overnight. Thereafter, blots were incubated with primary and secondary antibodies diluted in 5% BSA for one hour at room temperature. Primary antibodies used were against ADAMTS4 (PA1-1750, Thermo Pierce Scientific, IL), versican full length (se-25831, Santa Cruz Biotechnology, CA) and versican fragments displaying the neo-epitope DPEEAE (ab19345, Abcam, Cambrigde, UK) resulting from ADAMTS cleavage by ADAMTS1/4 (Sandy J D et al. J Biol Chem 2001. 276(16):13372-8; Didangelos A et al. supra), and quantified by ImageJ.

Statistical Analyses

Data are reported as mean±SEM or median (interquartile range) for continuous variables depending on the distribution. For mRNA levels, data are normalized to RPL4 and control. For protein levels, data are normalized to control. Comparisons between groups were investigated with student t-test or Mann-Whitney test for continuous variables depending on the distribution. Dunn's correction was used for multiple comparisons for data from cell cultures. P-values (two-sided)≤0.05 were considered significant.

Results

Myocardial mRNA Levels of ADAMTS Versicanases are Increased in AB-Rats

The ADAMTS with known versicanase and aggrecanase activity were measured in left ventricles from AB rats (FIG. 1). ADAMTS1 mRNA level was ~1.7-fold higher in ABHF (1.74 (1.51-1.99)) than in both ABHT (0.95 (0.77-1.01), p<0.01) and sham (1.00 (0.80-1.30), p<0.01). Moreover, mRNA expression of ADAMTS4 was higher in ABHT (1.66 (1.44-4.02)) than in sham (1.00 (0.95-1.11), p=0.01), while the most pronounced elevation was found in the ABHF demonstrating ~9 times higher levels than sham (8.75 (3.97-38.21), p<0.01) and 5 times higher levels than ABHT (p<0.01). For ADAMTS20, mRNA expression was 1.7 times higher in ABHT (1.68 (1.53-2.21)) than in both sham (1.00 (0.83-1.33), p<0.01) and ABHF (1.00 (0.90-1.45), p<0.01). On the contrary, mRNA expression of ADAMTS5 mRNA expression was lower in ABHT (0.79 (0.70-0.91) than in sham (1.00 (0.89-1.14), p=0.02), with an even further decrease in ABHF rats (0.63 (0.56-0.82), ABHF vs sham p=0.03, ABHF vs ABHT p=0.05).

In addition, the mRNA expressions of ADAMTS8, -9, -15, -16, and -18, with known aggrecan cleavage properties, were quantified in AB rats. Compared to sham (1.00 (0.66-1.53)), the level of ADAMTS8 increased by ~6- and 10-fold in ABHT (5.67 (4.17-6-91), p<0.01) and ABHF (10.22 (7.00-19.36), p<0.01), respectively, where the level in ABHF was also significantly higher than ABHT (p=0.02). For ADAMTS15 a tendency to higher mRNA levels in ABHT (1.28 (1.08-1.51)) than in sham (1.00 (0.84-1.16), p=0.06) were observed, while no significant differences were measured in the ABHF group (1.26 (0.94-1.44), ABHF vs sham p=0.24, ABHF vs ABHT p=0.66). On the contrary, ADAMTS9 and -18 mRNA levels were unaltered following AB (ADAMTS9: sham 1.00 (0.82-1.14), ABHT 0.95 (0.81-1.12), ABHF 0.97 (0.73-1.65); ADAMTS18: sham 1.00 (0.68-1.45), ABHT 0.91 (0.50-1.08), ABHF 0.59 (0.54-1.04)). As for ADAMTS5, the mRNA expression of ADAMTS16 was lower in ABHF (0.58 (0.45-0.86)) than in sham (1.00 (0.69-1.31), p=0.05) and ABHT (1.08 (0.84-1.37), p=0.02), however, the ABHT levels did not differ from sham levels (p=0.51) (FIG. 1). For ADAMTS6, for which the substrate is yet to be determined, levels decreased after heart failure development, with a lower level in ABHF (0.58 (0.45-0.86)) than both in sham (1.00 (0.69-1.31), p=0.05) and ABHT (1.08 (0.84-1.37), p=0.02), however, the ABHT levels did not differ from sham levels (p=0.51). Baseline characteristics of AB-rats are given in Table 1.

Myocardial mRNA Level of Versican and Aggrecan are Increased in AB-Rats

Versican and aggrecan mRNA levels increased after AB (FIG. 2). Compared to versican levels in sham (1.00 (0.92-1.55), a 1.5-fold increase in ABHT (1.52 (1.26-2.31), p=0.03), and 3.5-fold increase in ABHF (3.46 (3.11-4.58), p<0.01) were observed. Similarly, aggrecan level increased 4-fold in ABHT (3.91 (2.57-6.39), p<0.01) and 6-fold in ABHF (5.78 (4.65-14.38), p<0.01) compared to sham levels (1.00 (0.57-1.30). However, we did not observe any incremental increase in aggrecan mRNA levels after transition to failure (ABHT vs ABHF: p=0.28).

Myocardial mRNA Level of Proteins Modulating ADAMTS Activity or Versican Function was Unaltered in AB-Rats Myocardial mRNA levels of TIMP-3, the endogenous inhibitor of ADAMTS4 (Hashimoto et al. FEBS Letter 2001. 494(3):192-5), were similar in all three AB groups (sham 1.00 (0.92-1.07), CH 1.18 (0.97-1.27), HF 0.97 (0.87-1.19)) (FIG. 3A). The mRNA level of MT4-MMP, which activates ADAMTS4 (Gao et al. J Biol Chem 2004. 279(11):10042-51), was higher in ABHT (0.89 (0.67-1.42)) than in ABHF (1.69 (1.21-2.29), p=0.05), and a tended towards higher levels in ABHF than in sham (1.00 (0.85-1.22), p=0.06), whereas the MT4-MMP levels did not differ between ABHT and sham (p=0.72) (FIG. 3B). A -3-fold and -5-fold increases in HAS-1 was observed in ABHT (2.56 (1.66-3.18), p<0.01) and ABHF (4.55 (3.98-9.11), p<0.01), respectively, compared to sham (1.00 (0.75-1.18), with a significant increase also between ABHT and ABHF (p<0.01). The mRNA level of HAS-2 was higher in ABHF (1.76 (1.37-2.82), p=0.01) than in sham (1.00 (0.66-1.33)), whereas levels in ABHT was not significantly different from neither sham (p=0.06) nor ABHF (p=0.10) (FIG. 3C).

ADAMTS4 and Versican mRNA Levels were Induced by Pro-Inflammatory Mediators in Cardiac Cells ADAMTS1 mRNA expression was lower in cardiac fibroblasts stimulated for 24 hours with LPS (0.52 (0.45-0.58), p<0.05), TNF-α alone (0.71 (0.60-0.85), p<0.05) and in combination with IL-1β (0.71 (0.69-0.73), p<0.05), than in control (1.00 (0.96-1.12) (FIG. 4A). Also TNF-α-stimulated cardiomyocytes (0.56 (0.52-0.60)) showed lower levels of ADAMTS1 than control cells (1.00 (1.00-1.08), p<0.05) (FIG. 4D). ADAMTS4 mRNA levels, on the other hand, were -9 and -6-fold higher in LPS-(8.55 (8.08-9.62), p<0.05) and IL-1β-stimulated (6.25 (4.21-7.65), p<0.05) cells respectively, than in controls (1.00 (0.92-1.08)). However, the highest increase in ADAMTS4 fibroblast level was observed after synergistic stimulation with both TNF-α and IL-1β (16.42 (15.41-17.63), p<0.05), where mRNA expression was ~16-fold higher than in non-stimulated cells (FIG. 4B). In cardiomyocytes, only the combination of IL-1β and TNF-α induced increased level of ADAMTS4 (2.98 (2.33-4.17) compared to control (1.00 (0.97-1.10), p<0.05) (FIG. 4E).

Interestingly, also versican mRNA expression increased following stimulation with inflammatory mediators. In cardiac fibroblasts, versican level increased in response to LPS (3.31 (2.25-3.99), p<0.05), IL-1β alone (2.28 (1.67-3.34), p<0.05) and in combination with TNF-α (5.06 (5.00-5.21), p<0.05) compared to control (2.28 (1.67-3.34)) (FIG. 4C). In cardiomyocytes, IL-1β alone (3.47 (3.34-3.71), p<0.05) and combined with TNF-α (7.04 (6.67-7.75), p<0.05), induced versican synthesis (control 1.01 (0.93-1.02)) (FIG. 4F).

PPS-Treatment Reduced ADAMTS4 mRNA Levels

ADAMTS1 and -4 versicanases were upregulated in ABHF. ADAMTS4 was considered to be a suitable target due to the considerable increase in both ABHT- and ABHF-rats, and inflammation-induced increase in cardiac cells. PPS has known ADAMTS4 inhibitory effects (Troeberg et al. FASEB J. 2008. 22(10):3515-24; Takizawa et al. FEBS Letter 2008. 582(19):2945-9) and was thus chosen as an ADAMTS4-inhibitor in AB-rats.

ADAMTS4 mRNA levels were reduced in AB-rats treated with PPS (1.29 (1.00-6.45)) compared to vehicle-treated AB-rats (6.03 (3.79-12.76), p=0.03) (FIG. 5). The mRNA levels of ADAMTS1, -5, -8, versican, aggrecan, HAS-1, HAS-2, TIMP-3 and MT4-MMP were not affected by PPS-treatment (FIG. 7). In the protein fractions, level of ADAMTS4 was not altered after PPS-treatment (data not shown).

PPS-Treatment Inhibited Myocardial Versican Cleavage in AB-Rats

Proteins were separated into three fractions for analysis of the presence of versican breakdown products; NaCl-soluble extracellular proteins (NaCl-ECM) and guanidine-soluble extracellular proteins (G-ECM), containing the fluid and matrix compartment of ECM respectively, in addition to cellular and cell-linked proteins dissolvable in SDS (SDS-samples) (FIG. 6D).

Presence of versican breakdown products were examined by immunoblotting using an antibody detecting the neo-epitope DPEAAE displayed after cleavage by ADAMTS1/4, where fragments of 150 and 70 kDa results from cleavage of the V0 and V1 isoform, respectively (FIG. 6E) (Sandy et al. supra, Didangelos et al. supra).

In NaCl-ECM, we observed a higher amount of p150 versican in vehicle-treated AB (2.14 (1.34-3.55)) than in vehicle-treated sham (1.06 (0.73-1.30), p=0.04). Following PPS-treatment, the levels of p150 versican in NaCl-ECM were halved (1.08 (0.69-1.63)) compared to vehicle-treated AB-rats (p=0.05) (FIG. 6A).

In G-ECM, the p70 versican fragment level was lower in vehicle-treated AB (0.67 (0.52-0.94)) than in vehicle-treated sham (1.02 (0.96-1.29), p=0.03), remaining significant after normalization to Coomassie (p=0.02). PPS-treatment reduced this fragment in PPS-treated sham (0.34 (0.28-0.61)) compared to vehicle-treated sham (1.02 (0.96-1.29), p=0.01) (FIG. 6B), although this difference did not remain significant after normalization to Coomassie (p=0.20). Furthermore, a higher level of full-length versican (p400) was measured in PPS-treated AB-rats (1.17 (0.77-6.85)) compared to vehicle-treated AB-rats (0.47 (0.41-0.92), p=0.03), remaining significant after normalization to Coomassie (0.02) (FIG. 6C).

Improved Heart Function in Aortic Banding Rats Treated with Pentosan Polysulfate PPS-treated AB-rats demonstrated enhanced contractile function compared to vehicle-treated rats (Table 2 and FIG. 8). Briefly, we observed a 23% higher fractional shortening in PPS-treated compared to vehicle-treated AB-rats. Furthermore, left ventricular diameter in systole in PPS-treated AB-rats constituted only three quarters of the diameter observed in vehicle-treated AB-rats, and a tendency towards lower lung weight in PPS-treated AB-rats were observed.

Discussion

In this study, it has been found that inhibition of ADAMTS4 improves systolic function in response to pressure overload. The findings suggest that this beneficial effect of PPS is mediated through a reduction in ADAMTS4 versicanase activity. This conclusion is based on the following main findings 1) increased ADAMTS4 mRNA levels and altered ADAMTS-induced versican degradation during heart failure development, 2) inflammation-induced ADAMTS4 and versican increase in cardiac cells, and 3) improved contractile performance, simultaneously with indications of reduced ADAMTS4 versicanase activity, in AB-rats receiving the ADAMTS4-inhibitor PPS. In summary, these findings shed light on a novel mechanism for heart failure development, and a promising novel heart failure therapy.

Enhanced ADAMTS Activity During Heart Failure Development

This study demonstrates several indications of an accelerated activity of ADAMTS versicanases and aggrecanases during heart failure development. First, in the myocardium of AB-rats, an increase in mRNA synthesis of ADAMTS1-, -4 and -8 was observed, concurrent with an increase in the ADAMTS4 activating enzyme MT4-MMP. In addition, the mRNA synthesis of versican and aggrecan accelerated, providing substrate for an increased ADAMTS-mediated degradation. Interestingly, the synthesis of ADAMTS4 and versican in cardiac cells was induced by TNF-α and IL-1β, cytokines found in enhanced levels in the failing myocardium (Torre-Amione et al. Circulation 1996. 93(4):704-11; Shioi et al. Circ Res 1997 81(5):664-71), thus suggesting inflammation as the trigger for ADAMTS-mediated versican degradation during pressure overload.

The notion of accelerated ADAMTS-induced versicanase activity in response to pressure overload, was supported by increased amount of versican p150 DPEEAE fragments resulting from ADAMTS-induced cleavage. In AB-rats, the amount of this versican proteolytic fragment doubled in the NaCl-ECM, which contains interstitial fluid dissolvable in saline. Interestingly, knowledge about the structure of ADAMTS4 provides clues to where the enzyme is located within the ECM. ADAMTS4 is namely the only enzyme in this family lacking a thrombospondin repeat tail, a structural feature known to link the ADAMTS enzyme to other ECM components (Apte et al. J Biol Chem 2009 284(46):31493-7). Therefore, ADAMTS4 could be expected to be located in the easily dissolvable NaCl-soluble ECM, providing further support to that the accumulation of p150 versican fragments is a result of accelerated ADAMTS4 activity.

Pentosan Polysulfate Reduced ADAMTS4 Versicanase Activity

PPS-treatment of AB-rats counteracted several of the alterations in ADAMTS4 and versican fragment levels observed in the vehicle-treated AB-rats. Previous studies have demonstrated that PPS inhibits aggrecanase activity of ADAMTS4 and -5 (Troeberg et al. supra) without affecting gene expression of the protease (Takizawa et al. supra). However, in the present study reduced mRNA levels of ADAMTS4 were observed after PPS-treatment, whereas the protein levels remained unchanged. Simultaneously, the mRNA level of the endogenous inhibitor TIMP-3 was not affected by PPS-treatment. A downregulation of p150 DPEEAE versican fragments in NaCl-ECM following PPS-treatment of AB-rats further supports that inhibition of ADAMTS4 versicanase activity by PPS was achieved.

PPS-Treatment Improved Contractile Function in AB-Rats

PPS-treatment of AB-rats slowed development of systolic dysfunction, halting the critical phase of transition to failure. The present study indicates that the beneficial effect of ADAMTS4-inhibition relates to the observed reduction in versican p150 fragments after PPS-treatment.

Without wishing to be bound by theory, the present findings suggest that an accelerated versicanase activity of ADAMTS4 leads to an accumulation of hydrophilic versican fragments, increasing the water content in the NaCl-soluble ECM. Myocardial edema is a feature of the failing heart (Brooks et al. Genomics 2010 95(2):84-92), suggested to be associated with systolic dysfunction (Abdel-Aty et al. Int J Cardiol 2009. 132(2):291-3; Laine et al. Circ Res 1991. 68(6):1713-1; Davis et al. J Appl Physiol 1995. 78(1):132-7). During the repetitive cycles of contraction and relaxation, moving of increased amounts of viscous interstitial fluid could compromise efficient contractions (Dongaonkar et al. Cardiovasc Res 2010 87(2):331-9). Excess interstitial water content may also lead to a decline in oxygen delivery, for instance by altering the tissue structure and increasing the distance between cells. Thus, counteracting the accumulation of versican fragments in the interstitial fluid may inhibit development of systolic dysfunction.

Clinical Implications

In view of the present study, ADAMTS enzymes, particularly ADAMTS4, represent a promising novel therapeutic target in patients with cardiac remodeling or heart failure, patients suspected of having cardiac remodeling or heart failure, or patients at risk of developing cardiac remodeling or heart failure. PPS has FDA-approval, and is used in treatment of interstitial cystitis, and osteoarthritis in veterinary medicine. PPS is well tolerated, and besides a mild anti-coagulative effect, PPS exerts few side effects. Thus, PPS (and other inhibitors of ADAMTS proteoglycanases) holds promise as a novel therapeutic agent for cardiac remodeling and/or in heart failure.

TABLE 1

Echocardiographic analyses and organ weights in AB-rats

| | SHAM (n = 9) | AB CH (n = 10) | AB HF (n = 6) |
|---|---|---|---|
| ORGAN WEIGHTS | | | |
| Body wt (g) | 367 ± 6 | 331 ± 13* | 329 ± 12† |
| Heart wt (g) | 0.99 ± 0.03 | 1.61 ± 0.07* | 2.77 ± 0.13*† |
| LV wt (g) | 0.52 ± 0.02 | 0.96 ± 0.04* | 1.34 ± 0.06*† |
| RV wt (g) | 0.15 ± 0.01 | 0.15 ± 0.01 | 0.33 ± 0.04*† |
| Lung wt (g) | 1.05 ± 0.07 | 1.56 ± 0.06* | 3.82 ± 0.19*† |

TABLE 1-continued

Echocardiographic analyses and organ weights in AB-rats

|  | SHAM (n = 9) | AB CH (n = 10) | AB HF (n = 6) |
|---|---|---|---|
| M-MODE LV | | | |
| IVSd (mm) | 1.46 ± 0.04 | 2.34 ± 0.09* | 2.47 ± 0.03* |
| LVDd (mm) | 6.25 ± 0.14 | 5.90 ± 0.26 | 7.65 ± 0.30*† |
| LVDs (mm) | 2.69 ± 0.16 | 2.44 ± 0.29 | 4.66 ± 0.32*† |
| FS (%) | 57 ± 2 | 59 ± 3.0 | 39 ± 3*† |
| PWd (mm) | 1.62 ± 0.04 | 2.41 ± 0.06* | 2.54 ± 0.05* |
| M-MODE AO/LA | | | |
| LAD (mm) | 3.42 ± 0.06 | 4.33 ± 0.08* | 6.57 ± 0.37*,** |
| Aorta (mm) | 2.53 ± 0.04 | 2.57 ± 0.03 | 2.58 ± 0.05 |
| DOPPLER | | | |
| Peak mitral flow (m s$^{-1}$) | 834 ± 34 | 842 ± 39 | 1094 ± 63*† |
| Mitral dec (m s$^{-1}$) | 2368 ± 149 | 3301 ± 208 | 5405 ± 437*† |
| Peak LVOT flow (m s$^{-1}$) | 1195 ± 62 | 960 ± 46* | 821 ± 152 |
| HR | 414 ± 8 | 421 ± 8 | 378 ± 7*† |
| Peak RVOT flow (m s$^{-1}$) | 947 ± 28 | 825 ± 18* | 727 ± 27*† |
| TISSUE DOPPLER | | | |
| Maximal velocity | 77 ± 3 | 52 ± 2* | 31 ± 1*† |
| Minimal velocity | 85 ± 3 | 44 ± 9* | 49 ± 3* |

AB, aortic banding; HT, hypertrophy; HF, heart failure; IVSd, interventricular septal end-diastolic dimension; LVDd, left ventricular diameter at end-diastole; LVDs, left ventricular diameter at end-systole; FS, fractional shortening; PWd, posterior wall dimension; LAD, left atrial diameter; LVOT, left ventricular outflow tract; CO, cardiac output; VTI, velocity-Eire integral; RVOT, right ventricular outflow tract; * vs sham, †p≤0.05 vs ABHT.

TABLE 2

Echocardiographic analyses and organ weights in PPS-treated aortic banding rats

|  | Sham ctr | Sham PPS | p sham ctr vs PPS | AB ctr | AB PPS | p AB ctr vs PPS | p sham ctr vs AB ctr | p sham ctr vs AB PPS |
|---|---|---|---|---|---|---|---|---|
| N | 7 | 5 |  | 16 | 16 |  |  |  |
| ORGAN WEIGHTS | | | | | | | | |
| Body wt (g) | 398 ± 13 | 408 ± 18 | 0.65 | 374 ± 8 | 363 ± 6 | 0.27 | 0.13 | 0.01 |
| Heart wt (g) | 1.14 ± 0.10 | 1.19 ± 0.11 | 0.74 | 1.85 ± 0.12 | 1.87 ± 0.09 | 0.88 | <0.01 | <0.01 |
| LV wt (g) | 0.66 ± 0.02 | 0.70 ± 0.03 | 0.38 | 0.98 ± 0.04 | 0.95 ± 0.07 | 0.65 | <0.01 | 0.02 |
| RV wt (g) | 0.17 ± 0.01 | 0.17 ± 0.01 | 0.89 | 0.19 ± 0.01 | 0.18 ± 0.01 | 0.80 | 0.38 | 0.36 |
| Lung wt (g) | 1.37 ± 0.04 | 1.41 ± 0.03 | 0.47 | 1.96 ± 0.19 | 1.64 ± 0.08 | 0.13 | 0.06 | 0.05 |
| M-MODE LV | | | | | | | | |
| IVSd (mm) | 1.50 ± 0.03 | 1.56 ± 0.04 | 0.30 | 2.05 ± 0.07 | 2.11 ± 0.06 | 0.48 | <0.01 | <0.01 |
| LVDd (mm) | 6.68 ± 0.24 | 6.89 ± 0.10 | 0.50 | 6.73 ± 0.13 | 6.53 ± 0.13 | 0.28 | 0.85 | 0.55 |
| LVDs (mm) | 3.09 ± 0.24 | 3.20 ± 0.41 | 0.82 | 3.51 ± 0.20 | 2.67 ± 0.12 | <0.01 | 0.24 | 0.09 |
| FS (%) | 53.7 ± 2.8 | 53.6 ± 5.8 | 0.99 | 48.0 ± 2.6 | 59.2 ± 1.5 | <0.01 | 0.21 | 0.07 |
| PWd (mm) | 1.57 ± 0.03 | 1.68 ± 0.08 | 0.18 | 2.05 ± 0.05 | 2.13 ± 0.06 | 0.29 | <0.01 | <0.01 |
| M-MODE AO/LA | | | | | | | | |
| LAD (mm) | 3.55 ± 0.08 | 3.68 ± 0.14 | 0.39 | 4.29 ± 0.19 | 4.18 ± 0.14 | 0.64 | 0.02 | <0.01 |
| Aorta (mm) | 2.64 ± 0.05 | 2.63 ± 0.04 | 0.88 | 2.52 ± 0.03 | 2.56 ± 0.03 | 0.30 | 0.02 | 0.13 |
| DOPPLER | | | | | | | | |
| Peak mitral flow (m/s) | 939 ± 40 | 946 ± 45 | 0.92 | 1088 ± 27 | 1069 ± 40 | 0.70 | <0.01 | 0.06 |
| Mitral dec (m/s) | 2710 ± 255 | 2368 ± 388 | 0.46 | 3877 ± 333 | 4415 ± 388 | 0.30 | 0.04 | 0.01 |
| Peak LVOT flow (m/s) | 1286 ± 90 | 1265 ± 107 | 0.88 | 1098 ± 77 | 899 ± 60 | 0.05 | 0.16 | <0.01 |
| HR | 437 ± 24 | 412 ± 11 | 0.42 | 405 ± 8 | 420 ± 6 | 0.14 | 0.12 | 0.36 |
| Peak RVOT flow (m/s) | 945 ± 49 | 911 ± 98 | 0.74 | 846 ± 31 | 938 ± 33 | 0.05 | 0.09 | 0.91 |
| TISSUE DOPPLER | | | | | | | | |
| Maximal velocity | 74.4 ± 5.4 | 72.9 ± 8.6 | 0.88 | 52.59 ± 3.40 | 50.70 ± 2.94 | 0.68 | <0.01 | <0.01 |
| Minimal velocity | 79.8 ± 4.3 | 82.4 ± 6.1 | 0.72 | 54.89 ± 2.83 | 59.06 ± 3.26 | 0.34 | <0.01 | <0.01 | wt, weight; LV, left ventricle; RV, right ventricle; IVSd, interventricular septal thickness at diastole; LVDd, left ventricular diameter at diastole; LVDs, left ventricular diameter at systole; PWd, posterior wall thickness at diastole; LAD, left atrial diameter; dec, decelleration; LVOT, left ventricular outflow tract; HR, heart rate; RVOT, right ventricular outflow tract.

EXAMPLE 2

Material and Methods
Ethics Statement

The experimental procedures conformed to the *European Convention for the Protection of Vertebrate Animals Used for Experimental and Other Scientific Purposes*. The protocols were approved by the Norwegian Council for Animal Research prior to the beginning of the study. All surgical procedures were performed in full anesthesia by an experienced investigator.

Animal Model

Male Wistar rats weighing 160-170 grams (approximately 7 weeks old) (Taconic, Skensved Denmark) underwent MI (myocardial infarction) by left coronary artery ligation as described previously (Sjaastad I, et al. *J Appl Physiol* 2000 October; 89(4):1445-54.). In all surgical procedures performed, a mixture of 67% $N_2O$, 28% $O_2$, and 4% isoflurane in an anesthesia chamber was used for preoperative sedation. To maintain anesthesia peroperatively, a mixture of 69% $N_2O$, 29% $O_2$, and 2% isoflurane was given by the endotracheal tube and the animals were ventilated on a respirator (Zoovent, Triumph Technical Services, Milton Keynes, UK). Buprenorphine (0.2 mg/kg) was given as postoperative analgesia after MI. Rats were housed in cages (one or two rats in each cage) with Bee Kay bedding (Scanbur B K, Nittedal, Norway) in 55% humidity on a 12 h light/dark cycle, with food pellets (RM1, 801151, Scanbur BK) and water ad libitum.

Animal Phenotyping and Administration of PPS in Myocardial Infarction Rat Model

At day 0 to 3 (median 2) after surgery, infarct size was quantified by echocardiography using the Vevo2100 system (Visualsonics Inc, Canada) and magnetic resonance imaging (MRi) using a 9.4 T/210 mm/ASR horizontal bore magnet (Agilent Technologies, Inc., USA). Initially, echocardiography was performed to select moderate to large infarcts ranging approximately 40 to 50%. Thereafter, infarct sizes were exactly measured by late-enhancement gadolinium MRi analyses (Bohl S., et al. American Journal of Physiology, 2009; 296 (4): H1200-H1208) and stratified into small infarcts (stratum 1: <43%, stratum 2: 43-48%), and large infarcts (stratum 3: 48-53%, stratum 4: >53%). The rats in each MI stratum and sham group were randomized to receive intervention or control treatment. The intervention group was treated with 6 mg/kg of sodium PPS (Interfarm AS, Norway), while the control group received vehicle (0.9% NaCl), both injected subcutaneously every third day starting from post-operative day 8-10. Rats were observed daily and no side effects including hemorrhage were observed.

After receiving PPS- or vehicle-treatment for 51 to 56 days (median 55 days), rats were sacrificed after examination by experienced investigators blinded to treatment group. In vivo heart function was evaluated as previously described with echocardiography (Sjaastad I, et al., *J Appl Physiol* 2000 October; 89(4):1445-54) and MRi (Espe E, *Journal of Cardiovascular Magnetic Resonance* 2013; 15(1):82). Thereafter, the heart and lung was excised under deep anesthesia, washed in saline and blotted dry to remove blood in the cardiac chambers. The heart chambers were separated by rapid dissection, before left ventricles were divided into infarcted and viable tissue. Lungs and cardiac tissue were snap-frozen in liquid nitrogen and stored at −70° C. until RNA and protein analyses.

RNA Isolation, Reverse Transcription and qRT-PCR

The mRNA levels of the ADAMTS versicanases ADAMTS1, -4, -5, -8, and -20 (Shiomi T, et al. Pathology International 2010; 60(7):477-96), versican, aggrecan, syndecan-4, tissue inhibitor metalloprotease (TIMP)-3, and membrane-type (MT)4-MMP, were quantified in rat left ventricle by qRT-PCR, as previously described in Example 1.

Fractional Protein Isolation, Immunoblotting, and Antibodies

Fractional protein lysates from myocardium of rats having undergone MI treated with PPS or vehicle were extracted as previously described in Example 1 and Didangelos et al. (*Journal of Biological Chemistry* 2012 Jun. 1; 287(23): 19341-5). Protein concentrations were measured by western blotting as previously described in Example 1. Primary antibody used was versican fragment displaying the neo-epitope DPEEAE resulting from cleavage by ADAMTS1/4 (Sandy J D et al., *Journal of Biological Chemistry* 2001 Apr. 20; 276(16):13372-8) (ab19345, Abcam, Cambridge, UK), and ADAMTS4 (PAI-175, Thermo Scientific, IL), and secondary antibody used was goat anti-rabbit IgG-HRP (4030-05, Southern Biotech, AL), diluted in 1% casein (versican DPEEAE and secondary antibody) or 5% non-fat dry-milk (170-6404, BioRad) (ADAMTS4). Membranes were blocked in 1% casein for one hour in room temperature, incubated overnight at 4° C. with primary antibody, and for one hour in room temperature with secondary antibody.

Statistical Analyses

Depending on the distribution, data are reported as mean±SEM or median (interquartile range) and comparisons between groups investigated with Student's t-test or Mann-Whitney test. p-values (two-sided)≤0.05 were considered significant. Data are normalized to RPL4 and vehicle-treated sham (mRNA) or vehicle-treated sham (protein).

Results and Discussion

Myocardial Infarction LED to Cardiac Remodeling and Heart Failure

The vehicle-treated MI rats included in the study had a remodeled heart and a pronounced failing phenotype, as shown by echocardiography, MRi, and necropsy measurements (Table 3). A higher heart weight and left ventricular diameter at diastole (end-diastolic diameter by MRi and left ventricular diameter at diastole by echocardiography) in vehicle-treated MI rats than in vehicle-treated shams were found, demonstrating hypertrophy and left ventricular dilatation, respectively (Table 3). Further comparisons of vehicle-treated shams to vehicle-treated MI rats, revealed an increase in left atrial diameter, right ventricular weight, and lung weight, confirming the heart failure phenotype of the vehicle-treated MI rats.

Myocardial Infarction Induced Changes in ADAMTS

Following MI, mRNA synthesis of the proteoglycanases ADAMTS1, -4, and -8 increased, accompanied by elevated levels of their substrates versican, aggrecan, and syndecan-4 (FIG. 9). Similarly, protein levels of the active form of ADAMTS4 and versican DPEEAE fragments specific for ADAMTS-induced cleavage, increased after MI (FIG. 10), supporting that enhanced ADAMTS proteoglycanase activity takes place during cardiac remodeling. Interestingly, the mRNA expression of MT4-MMP, which activates ADAMTS4, also increased after MI (FIG. 10), suggesting that regulation of MT4-MMP is one regulatory step in modulation of ADAMTS4-activity. These data corresponds well with our previous findings in PPS-treated aortic banding rats (Example 1), and demonstrate that regulation of ADAMTS-proteoglycanase activity applies to heart failure development in general, independent of the underlying etiology.

Improved Heart Function in MI-Rats Treated with PPS

In rats with large infarcts, PPS-treatment led to substantial reduction in parameters for heart failure, including a 1/3 reduction in lung weight, and a 10% reduction in left atrial diameter (Table 4 and FIG. 11). Inhibition of heart failure development after PPS-treatment was further supported by an improved velocity time integral and maximum systolic velocity after PPS-treatment. In addition, PPS-treated rats with large infarcts had a ~25% reduction in heart weight as compared to the corresponding vehicle-treated rats, further supporting a beneficial effect on cardiac remodeling.

Previously, a cardioprotective effect of reducing infarct size has been demonstrated of PPS during acute ischemia/reperfusion (Tanhehco E J, et al. *Journal of Cardiovascular Pharmacology* 1999; 34(1):153-61). However, in our study treatment was initiated after complete scarring and thinning of the infarct area, without possibility to affect infarct size. Thus, the beneficial effect of PPS-treatment in our study is achieved by slowing the cardiac remodeling and heart failure development that occurs in response to an unchanged infarct size.

PPS-Treatment Reduced Myocardial ADAMTS4 and -5 Levels

Interestingly, active ADAMTS4 protein levels, ADAMTS5 mRNA levels, and versican DPEEAE fragments, all decreased in response to PPS-treatment in MI rats (FIG. 10), demonstrating that PPS indeed inhibit ADAMTS versicanase activity. Moreover, mRNA levels of MT4-MMP, an enzyme that activates ADAMTS4, also decreased after PPS-treatment, indicating that regulation of this enzyme contributes to the ADAMTS4-inhibitory effect exerted by PPS. The endogenous inhibitor of ADAMTS4, TIMP-3, did not change in response to PPS-treatment, thus the balance between ADAMTS4 and its inhibitor suggests increased activity. In summary, our finding clearly indicates that PPS-treatment in MI rats reduces cardiac remodeling and heart failure development through inhibition of ADAMTS proteoglycanase activity, especially versicanase activity exerted by ADAMTS4.

TABLE 3

Characteristics of each vehicle-treated MI stratum compared to vehicle-treated sham

|  | Sham | MI stratum 1 | p | MI stratum 2 | p | MI stratum 3 | p | MI stratum 4 | p |
|---|---|---|---|---|---|---|---|---|---|
| N | 6 | 4 |  | 7 |  | 5 |  | 4 |  |
| ORGAN WEIGHTS |
| Heart (g) | 1030 (963-1123) | 1335 (1203-1490) | 0.02 | 1670 (1390-2072) | <0.01 | 1980 (1540-2050) | <0.01 | 2195 (2103-2288) | 0.01 |
| RV (g) | 180 (153-180) | 230 (213-278) | 0.01 | 280 (230-400) | <0.01 | 460 (350-540) | <0.01 | 485 (458-520) | 0.01 |
| Lung (g) | 1300 (1235-1423) | 1615 (1430-2003) | 0.04 | 2420 (1550-2960) | 0.01 | 4060 (2470-4255) | 0.03 | 4445 (4113-4913) | 0.01 |
| MAGNETIC RESONANCE IMAGING |
| Infarct size (%) | NA | 40.2 ± 0.0 |  | 46.0 ± 0.0 |  | 50.7 ± 0.0 |  | 56.5 ± 0.0 |  |
| EDV | 290 (239-322) | 509 (497-576) | 0.02 | 550 (528-714) | <0.01 | 665 (577-727) | <0.01 | 711 (587-807) | 0.02 |
| ECHOCARDIOGRAPHY |
| LVDd (mm) | 6.99 (6.71-7.31) | 8.85 (8.77-9.04) | 0.02 | 9.66 (9.24-10.24) | <0.01 | 10.29 (9.53-10.71) | <0.01 | 11.06 (10.72-11.77) | 0.01 |
| LAD (mm) | 3.80 (3.70-3.80) | 4.44 (4.33-4.60) | 0.02 | 6.64 (5.96-7.05) | <0.01 | 7.34 (5.88-7.68) | <0.01 | 8.05 (7.28-8.17) | 0.01 |
| VTI (mm) | 64.5 (51.9-71.2) | 65.5 (36.0-71.8) | 1.00 | 56.6 (50.1-65.7) | 0.45 | 48.4 (38.6-49.5) | 0.03 | 44.7 (38.8-54.7) | 0.07 |
| Max syst velocity | 67.2 (62.4-68.0)** | 37.3 (27.5-43.4)** | 0.10 | 34.0 (23.9-42.3)* | 0.06 | 30.0 (25.1-39.7) | 0.04 | 32.4 (28.3-38.9)** | 1.00 |

RV, right ventricle; EDV, end-diastolic volume; LVDd, left ventricular diameter at diastole; LAD, left atrial diameter; VTI, velocity time integral; max syst velocity, maximum systolic velocity; NA, not applicable

TABLE 4

Echocardiographic, MRI and organ weights after PPS-treatment in rats with large myocardial infarcts

|  | Sham veh | Sham PPS | p | MI strata 1 + 2 veh | MI strata 1 + 2 HF PPS |
|---|---|---|---|---|---|
| N | 6 | 6 |  | 11 | 11 |
| ORGAN WEIGHTS |
| Heart (mg) | 1030 (963-1123) | 1005 (980-1248) | 0.82 | 1440 (1320-1710) | 1610 (1450-1760) |
| RV (mg) | 180 (153-180) | 168 (160-208) | 1.00 | 240 (220-350) | 300 (180-345) |
| Lung (mg) | 1300 (1235-1423) | 1255 (1158-1280) | 0.31 | 1820 (1490-2910) | 1930 (1450-3420) |

TABLE 4-continued

Echocardiographic, MRI and organ weights after PPS-treatment in rats with large myocardial infarcts

| MAGNETIC RESONANCE IMAGING | | | | | |
|---|---|---|---|---|---|
| Infarct size (%) | NA | NA | — | 43.9 ± 0.0 | 43.1 ± 0.0 |
| EDV | 290 (239-322) | 293 (256-346) | 0.82 | 542 (513-649) | 614 (524-707) |

ECHOCARDIOGRAPHY

| | | | | | |
|---|---|---|---|---|---|
| LVDd (mm) | 6.99 (6.71-7.31) | 6.91 (6.60-7.88) | 1.00 | 9.34 (8.89-9.98) | 9.91 (9.50-10.29) |
| LAD (mm) | 3.80 (3.70-3.80) | 3.67 (3.45-3.73) | 0.18 | 6.31 (4.52-6.87) | 5.32 (4.25-6.50) |
| VTI (mm) | 64.5 (51.9-71.2) | 58.5 (53.9-65.5) | 0.70 | 59.8 (50.1-71.2) | 57.9 (50.8-69.6) |
| Max. syst velocity | 67.2 (62.4-68.0)** | 64.0 (46.6-67.2) | 0.57 | 37.3 (27.5-43.7)* | 39.7 (28.3-57.5) |

| | p | MI strata 3 + 4 veh | MI strata 3 + 4 PPS | p |
|---|---|---|---|---|
| N | | 9 | 11 | |

ORGAN WEIGHTS

| | | | | |
|---|---|---|---|---|
| Heart (mg) | 0.48 | 2050 (1885-2195) | 1595 (1475-1710) | 0.01 |
| RV (mg) | 0.75 | 480 (455-530) | 395 (355-523) | 0.28 |
| Lung (mg) | 0.70 | 4080 (3845-4510) | 2770 (1990-3385) | <0.01 |

MAGNETIC RESONANCE IMAGING

| | | | | |
|---|---|---|---|---|
| Infarct size (%) | 0.59 | 53.3 ± 0.0 | 52.7 ± 0.0 | 0.73 |
| EDV | 0.40 | 678 (592-750) | 644 (552-709) | 0.67 |

ECHOCARDIOGRAPHY

| | | | | |
|---|---|---|---|---|
| LVDd (mm) | 0.10 | 10.67 (10.18-11.15) | 10.25 (9.51-10.75) | 0.32 |
| LAD (mm) | 0.46 | 7.61 (6.90-8.05) | 6.88 (5.51-7.31) | 0.05 |
| VTI (mm) | 1.00 | 48.4 (39.0-50.0) | 69.8 (51.1-75.9)* | <0.01 |
| Max. syst velocity | 0.33 | 30.8 (28.7-37.3)* | 41.7 (31.2-52.0)* | 0.08 |

RV, right ventricle; EDV, end-diastolic volume; LVDd, left ventricular diameter at diastole; LAD, left atrial diameter; VTI, velocity time integral; max syst velocity, maximum systolic velocity; NA, not applicable; veh, vehicle

What is claimed is:

1. A method for treating left ventricular remodeling or chronic heart failure in a subject comprising administering a therapeutically effective amount of an inhibitor of ADAMTS4 or ADAMTS5 to a subject having left ventricular remodeling or chronic heart failure,
    wherein said subject is further characterized by having, or being suspected of having, a condition selected from the group consisting of cardiomyopathies, heart valve disease, heart valve dysfunction, hypertension, pulmonary hypertension, congenital heart disease, arrhythmias, and coronary artery disease, or wherein said subject has undergone myocardial infarction,
    and wherein said inhibitor of ADAMTS4 or ADAMTS5 is not marimastat.

2. The method of claim 1, wherein said inhibitor is an inhibitor of ADAMTS4.

3. The method of claim 1, wherein said inhibitor reduces the functional activity of ADAMTS4 or ADAMTS5 thereby decreasing the amount of versican cleavage products and/or decreasing the amount of aggrecan cleavage products in the subject.

4. The method of claim 1, wherein said inhibitor is a selective inhibitor.

5. The method of claim 1, wherein said inhibitor is pentosan polysulfate.

6. The method of claim 1, wherein said subject is in the chronic phase of a disease or condition.

7. The method of claim 1, wherein said subject is in the chronic phase after myocardial infarction.

8. The method of claim 1, wherein if a subject has undergone myocardial infarction said treating is initiated at least two days after myocardial infarction.

9. The method of claim 1, wherein if a subject has undergone myocardial infarction said treating is initiated after complete scarring and thinning of the infarct area.

10. The method of claim 1, wherein said subject has signs of cardiac remodeling.

11. The method of claim 1, wherein said subject is further characterized by having aortic stenosis or wherein said subject has undergone myocardial infarction.

12. The method of claim 1, wherein heart failure is treated.

13. The method of claim 1, wherein said heart valve disease is aortic heart valve disease.

14. The method of claim 13, wherein said aortic heart valve disease is aortic valve insufficiency, aortic valve regurgitation or aortic stenosis.

* * * * *